US006171787B1

(12) United States Patent
Wiley

(10) Patent No.: US 6,171,787 B1
(45) Date of Patent: *Jan. 9, 2001

(54) MEMBER OF THE TNF FAMILY USEFUL FOR TREATMENT AND DIAGNOSIS OF DISEASE

(75) Inventor: Steven R. Wiley, Libertyville, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/883,086

(22) Filed: Jun. 26, 1997

(51) Int. Cl.[7] .................................................. C12Q 1/68
(52) U.S. Cl. ...................... 435/6; 536/23.1; 536/23.5; 536/24.3; 536/24.31; 536/244.33; 536/25.3; 435/91.2
(58) Field of Search ................. 435/6, 91.2; 536/23.1, 536/24.33, 24.3, 25.3, 24.31, 23.5

(56) References Cited

U.S. PATENT DOCUMENTS

| 5,563,036 | 10/1996 | Peterson et al. . |
| 5,563,039 | 10/1996 | Goeddel et al. . |

FOREIGN PATENT DOCUMENTS

| 9213951 | 8/1992 | (WO) . |
| 9316178 | 8/1993 | (WO) . |
| 9614328 | 5/1996 | (WO) . |
| 9701633 | 1/1997 | (WO) . |
| 9733902 | 9/1997 | (WO) . |
| 9835061 | 8/1998 | (WO) . |

OTHER PUBLICATIONS

Cross et al. Naturegenet. 6(3): 236–244.*
Fisher et al., *Cell*, vol. 81, pp. 935–946 (1995).
Gray et al., *Nature*, vol. 312, pp. 721–724 (1984).
Hernandez–Caselles et al., *The Journal of Immunology*, vol. 151, pp. 3999–4012 (1993).
Pennica et al., *Nature*, vol. 312, pp. 724–729 (1984).
Smith et al., *Cell*, vol. 73, pp. 1349–1360 (1993).
Smith et al., *Cell*, vol. 76, pp. 959–962 (1994).
Wiley, S. R., et al., "Identification and Characterization of a New Member of the TNF Family that induces Apoptosis", *Immunity*, 3:673–682 (1995).
Hiller, L. et al., "zu35f06.rl Soares ovary tumor NbHOT homosapiens cDNA clone 740003 3", *Access. #AA477087*, (91997).
Hiller, L., et al., "zv45c01.sl Soares tumor NbHOT Homosapiens cDNA clone 756576.3", *Access. #AA481449*, (1977).
Adams, M., et al., "EST71241 T–cell lymphoma Homosapiens cDNA 5' end.", *Access. #AA361896*, (1997).

* cited by examiner

*Primary Examiner*—Jennifer Graser
(74) *Attorney, Agent, or Firm*—Cheryl L. Becker; Mimi C. Goller

(57) ABSTRACT

An isolated clone consisting of sequences transcribed from the TNF-gamma gene. Also provided are human polypeptides translated from said TNF-gamma sequences and a procedure for producing such polypeptide by recombinant techniques. Also provided are a procedure for producing soluble biologically active TNF-gamma, which may be used to treat deficiencies of TNF-gamma and diseases conditions ameliorated by TNF-gamma. Antibodies, antagonists and inhibitors of such polypeptide which may be used to prevent the action of such polypeptide and therefore may be used therapeutically to treat TNF-gamma associated diseases, tumors or metastastases are disclosed. Also disclosed is the use of said antibodies, agonists and inhibitors as well as the nucleic acid sequences to screen for, diagnose, prognosticate, stage and monitor conditions and diseases attributable to TNF-gamma, especially inflammation. The use of said partial sequence to provide antibodies, agonists and inhibitors as well as partial nucleic acid sequences to screen for, diagnose, stage and monitor diseases associated with TNf-gamma, including but not limited to inflammation. Illustrative sequences and clone designations for TNF-gamma are provided.

6 Claims, 2 Drawing Sheets

```
hTNF-gamma  115 ----------------HSVLHLVPINATSKDDDVTE---  135
hTNFa        87 ----------------KPVAHVVANPQAEGQ-------  101
mTNFa        90 ----------------KPVAHVVAHQVEEQ--------  104
hTNFb        62 ----------------KPAAHLIGDPSKQNS-------   76
hLTb         87 ----------------LPAAHLIGAPIKGQG-------  101
hTRAIL      109 NISPLVRERGPQRVAAHITGTRGRSNTLSSPNSKNE    144 hTNF-gamma  136 -------VMWQPALRBGR---GLQAQGY--GVRIQDA   160
hTNFa       102 -------LQWLNRRANALLANGVELRDN-QLVVPSE    129
mTNFa       105 -------LEWLSQRANALLANGMDLKDN-QLVVPAD    132
hTNFb        77 -------LRWLRANTDRAFLQDGFSLSNN-SLLVPTS   104
hLTb        102 -------LGWETTKEQAFLTSGTQFSDAEGLALPQD    130
hTRAIL      145 KALGRKINSWESSRSGHSFLSNLHLRNG-ELVIHEK   179 hTNF-gamma   16 GVYLLYSQVLFQDV-------TFTMGQVVSRE       185
hTNFa       130 GLYLIYSQVLFKGQGCPST--HVLLTHTISRI       159
mTNFa       133 GLYLVYSQVLFKGQGCPD---YVLLTHTVSRF       161
hTNFb       105 GIYFVYSQVVFSGKAYSPKATSS--PLYLAHEVQLF   138
hLTb        131 GLYYLYCLVGYRGRAPPGGGDPQGFSVTLRSSLYRA   166
hTRAIL      180 GFYYIYSQTYFRFQEEIKEN----TKNDKQMVQYI    210
```

FIG. 1A

```
hTNF-gamma  186  G----QRQETL FRCIRSMPSH PDR---------AY  208
hTNFa       160  A---VSYQTKVNLL SAIKSPCQ FETPEGAEAKP---WY  191
mTNFa       162  A---ISYQEKVNLL SAVKSPCPKDTPEGAELKP---WY  193
hTNFb       139  S---SQYPFHVPLL SSQKMVYPGIQEP-------WL  164
hLTb        167  GGAYGPGTPELL LEGAETVTPVID PARRQGYGPLWY  202
hTRAIL      211  YKYTSYPDPILL MKSARNSCWSK DAEY--------GL  239 hTNF-gamma  209  NSCYSAGVFHL HQGDILSVI IPRARAKL NLSPH-GT  243
hTNFa       192  EPIYLGGVFQL EKGDRLSAEINR-PDYLDFAESGQV  226
mTNFa       194  EPIYLGGVFQL EKGDQSAEVNL-PKYLDFAESGQV  228
hTNFb       165  HSMYHGAAFQL IQGDQLSTIHTDG-IPHLVLSPS-TV  198
hLTb        203  TSVGFGGLVGLRRGERVYVNISH-PDMVDFARG-KT  236
hTRAIL      240  YSIYQGGIFEL KENDRIFVSVT--NEHLIDMDHEAS  273 hTNF-gamma  244  FLGFVKL-              250
hTNFa       227  YFGIIAL-              233
mTNFa       229  YFGVIAL-              235
hTNFb       199  FFGAFAL-              205
hLTb        237  FFGAVMVG              244
hTRAIL      274  FFGAFLMG              281
```

FIG. 1B

MEMBER OF THE TNF FAMILY USEFUL FOR TREATMENT AND DIAGNOSIS OF DISEASE

BACKGROUND OF THE INVENTION

This invention relates generally to extracellular signal molecules, and more particularly, relates to a member of the tumor necrosis factor (TNF) family of molecules designated as TNF-gamma, reagents and methods for its detection as well as its use in therapeutics.

The TNF (tumor necrosis factor) family is an expanding set of extracellular signaling molecules (ligands) with biological activities that are intimately associated with a variety of disease conditions. The prototypic member of this family, TNF, is well known as a mediator of septic shock, inflammation, and graft verse host disease. See, for example, A. Cerami, *Immunol Today,* 9:28–31 (1988); M. Revel, *Ciba Found Symp,* 129:223–33 (1987); J. Cohen, *J. Bone Marrow Transplant* 3(3):193–197 (1988). Also, because of its beneficial effects on vasculature of solid tumors, isolated perfusion of TNF is being evaluated as a therapeutic agent for cancer patients. M. W. Boehme, *Eur. J. Clin. Invest.* 26: 404–410 1996).

The important role of the TNF family in immune regulation has been demonstrated by mutations both in mice and humans. For instance, mice with a loss of function mutation in the TNF family member known as Fas ligand present a variety of disorders including lymphadenopathy and autoimmune disease . See, for example, R. Watanabe-Fukunaga, *Nature* 356:314–317 (1992); Takahishi et al., *Cell* 76:969–966, (1994), Adiachi et al, *PNAS,* 90:1756 (1993); Fisher et al, *Cell* 81:953–946 (1995); F. Rieux-Laucat, *Science* 268:1347 (1995). Another example of the immune regulation role is mutation of the TNF family member CD40 ligand in humans. Spontaneous CD40 ligand mutations in human patients result in hyper Ig-M syndrome, demonstrating the requirement of CD40 ligand for B-cell maturation and isotype switching. Also, targeted disruption of TNF family member LTa in mice results in failure to develop peripheral lymph nodes. P. De Togni, *Science* 264:703–707 (1994).

Another property of this family of ligands which is potentially clinically useful is the ability to selectively induce apoptosis (programmed cell death) in a variety of cancer cells, but not in most normal cells. The two known members of the TNF family which induce apoptosis in the widest variety of cell lines are TRAIL (TNF related apoptosis inducing ligand) and Fas ligand. See, for example, T. Suda et. al., *Cell* 75:1169–1178 (1993); Wiley et. al., *Immunity* 3:673–682, (1995). This property is unique to the TNF family of ligands.

Members of the TNF family of ligands can be identified by a region of amino acid conservation which is approximately restricted to the N-terminal 150 amino acids. This region forms a b-pleated sheet structure which trimerizes and interacts with the cognate receptors. Within this N-terminal domain there are isolated regions of homology which correspond to the strands of the beta-pleated sheet. Therefore, the total amino acid sequence identity between TNF family members is not high, but can be recognized by those skilled in the art.

Given the crucial roles members of this family of molecules in immune regulation, investigation into the existence and identity of other members of the TNF family is desirable. The identification and characterization of these molecules provide means to identify and treat a variety of immune disorders.

SUMMARY OF THE INVENTION

The present invention provides a novel member of the TNF family of ligands, as well as isolated DNA encoding the complete protein sequence of this novel member, and expression vectors encoding a soluble form of this novel member. Since this novel member of the TNF family is more closely related to TNF-alpha than any other member of the family, it is designated TNF-gamma.

A method for producing TNF-gamma polypeptides involves expression in host cells transformed with a recombinant expression vector that contains an engineered soluble version of TNF-gamma, as well as a cell surface expressed form of TNF-gamma.

The present invention also provides a method of detecting target polynucleotides of TNF-gamma in a test sample which comprises contacting a target polynucleotide specific for TNF-gamma with at least one TNF-gamma specific polynucleotide and fragment or complement thereof provided herein and detecting the presence of the target in the test sample. The polynucleotide comprises SEQUENCE ID NO 1 and fragments or complements thereof. Also, the TNF-gamma polynucleotide may be attached to a solid phase prior to a performing the assay.

The present invention also provides a method for amplifying 5' end cDNA of TNF-gamma gene in a test sample, which comprises performing reverse transcription with random primers, amplifying the cDNA obtained by using other oligonucleotide primer(s) of TNF-gamma as sense and anti-sense primer(s) in a first-stage PCR to obtain amplified cDNA and detecting the presence of TNF-gamma amplicon in the test sample. Amplification can be performed by the polymerase chain reaction. Also, the test sample can be attached to a solid phase prior to performing the method. Further, the detection step can comprise utilizing a detectable label capable of generating a measurable signal. The detectable label can be attached to a solid phase.

The present invention further provides a method of detecting TNF-gamma in a test sample suspected of containing TNF-gamma, which comprises contacting said test sample with at least one polynucleotide as a sense primer and with at least one polynucleotide as an anti-sense primer and amplifying same to obtain a first stage reaction product; contacting said first stage reaction product with at least one of said polynucleotides of the contacting step and a second polynucleotide, with the proviso that the second oligonucleotide is located 3' to the first oligonucleotide utilized and is of opposite sense to said first oligonucleotide and detecting said TNF-gamma as an indication of the presence of disease. The amplification may be performed by the polymerase chain reaction. The test sample can be attached to a solid phase prior to performing the method. The detection step also comprises utilizing a detectable label capable of generating a measurable signal, and the detectable label can be attached to a solid phase. Test kits useful for detecting TNF-gamma target in a test sample further are provided which comprise a container containing at least one polynucleotide selected from the group consisting of SEQUENCE ID NO 1, and fragments or complements thereof. These test kits further comprising containers containing tools useful for collecting test samples such as blood, urine, saliva, and stool. Such tools include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. These items also may be treated with or contain preservatives, stabilizers or antimicrobial agents to help maintain the integrity of the specimens.

The present invention provides a purified polynucleotide or fragment thereof derived from TNF-gamma gene capable of selectively hybridizing to the genomic TNF-gamma gene or the complement thereof. The polynucleotide is selected from the group consisting of SEQUENCE ID NO 1, and fragments or complements thereof. Further, the polynucleotide can be produced by recombinant techniques. This recombinant polynucleotide comprises a sequence that encodes at least one epitope of TNF-gamma and is contained within a recombinant vector. The recombinant polynucleotide further comprises a host cell transformed with said vector.

The present invention further provides a recombinant expression system comprising an open reading frame of DNA or RNA derived from TNF-gamma gene wherein said open reading frame comprises the test sample with at least one TNF-gamma specific polynucleotide or complement thereof, and detecting the presence of the target polynucleotide of TNF-gamma in the test sample. The TNF-gamma specific polynucleotide has at least 50% identity to polynucleotide SEQUENCE ID NO 1 and fragments, analogs or complements thereof. The target polynucleotide of TNF-gamma can be attached to a solid phase prior to performing the method.

The present invention also includes a method for detecting mRNA of TNF-gamma in a test sample, which comprises (a) performing reverse transcription with at least one primer in order to produce cDNA; (b) amplifying the cDNA obtained from step (a) by using other oligonucleotide primer (s) of TNF-gamma as sense and antisense primer(s) in a first-stage amplification to obtain TNF-gamma amplicon; and (c) detecting the presence of TNF-gamma amplicon in the test sample, wherein the oligonucleotide primers of TNF-gamma have at least 50% identity to SEQUENCE ID NO 1 and fragments, analogs or complements thereof. The method further comprises reacting the test sample with a solid phase prior to performing step (a) or step (b) or step (c). Further, the detection step can further comprise utilizing a detectable label capable of generating a measurable signal.

An additional method is provided for detecting target TNF-gamma polynucleotide in a test sample suspected of containing the target. This method comprises (a) contacting the target TNF-gamma polynucleotide with at least one TNF-gamma oligonucleotide as a sense primer and with at least one TNF-gamma oligonucleotide as an anti-sense primer and amplifying same to obtain a first stage reaction product; (b) contacting said first stage reaction product with at least one other TNF-gamma oligonucleotide, with the proviso that the other TNF-gamma oligonucleotide is located 3' to the TNF-gamma oligonucleotides utilized in step (a) and is complementary to the first stage reaction product; and (c) detecting the target TNF-gamma polynucleotide, wherein the TNF-gamma oligonucleotides utilized in step (a) and step (b) have at least 50% identity to SEQUENCE ID NO 1 and fragments, analogs or complements thereof. Further, the test sample can be reacted with a solid phase prior to performing step (a) or step (b) or step (c). Also, the detection step can comprise utilizing a detectable label capable of generating a measurable signal. Further, the detectable label can be attached to a solid phase.

The present invention further provides a test kit useful for detecting TNF-gamma polynucleotide in a test sample, comprising a container containing at least one TNF-gamma polynucleotide having at least 50% identity to SEQUENCE ID NO 1 and fragments, analogs or complements thereof. Further, the test kit comprises a container containing tools useful for collection of said sample selected from the group consisting lancets, absorbent paper, cloth, swabs and cups.

A purified polynucleotide or fragment thereof derived from TNF-gamma gene also is provided. The purified polynucleotide is capable of selectively hybridizing to the nucleic acid of said TNF-gamma gene, and the purified polynucleotide has at least 50% identity to SEQUENCE ID NO 1 and fragments, analogs or complements thereof. Further, the purified polynucleotide can be produced by recombinant techniques. When produced by recombinant techniques, the purified polynucleotide further can comprise a sequence of at least one epitope encoded by TNF-gamma.

The present invention provides a recombinant expression system comprising a nucleic acid sequence that encodes an open reading frame derived from TNF-gamma which is operably linked to a control sequence compatible with a desired host. The nucleic acid sequence has at least 50% identity to SEQUENCE ID NO 1 and fragments, analogs or complements thereof. This recombinant expression system further comprises a cell transformed with the recombinant expression system.

The present invention further provides a polypeptide encoded by TNF-gamma. The polypeptide has at least 35% identity to amino acid sequence selected from the group consisting of SEQUENCE ID NO 2, SEQUENCE ID NO 3, and fragments thereof. The polypeptide can be produced by recombinant technology or by synthetic techniques.

A compound which inhibits activation of the TNF-gamma polypeptide is provided. The TNF-gamma polypeptide has at least 35% identity to an amino acid sequence selected from the group consisting of SEQUENCE ID NO 2, SEQUENCE ID NO 3 and fragments thereof. The invention further provides a polypeptide as a soluble fragment of the TNF-gamma protein which is capable of binding a receptor for TNF-gamma.

A method for treating a patient having a need to induce activation of the TNF-gamma polypeptide is provided, which comprises administering to the patient a therapeutically effective amount of a compound which induces activation of the TNF-gamma polypeptide. TNF-gamma polypeptide has at least 35% identity to an amino acid sequence selected from the group consisting of SEQUENCE ID NO 2, SEQUENCE ID NO 3, and fragments thereof.

The present invention provides a method for determining whether a compound is an agonist or antagonist to TNF-gamma protein. This method comprises (a) contacting a cell having TNF-gamma protein expressed on its surface with said compound and a receptor ligand; (b) determining whether a biological effect is produced from the interaction of the ligand and the receptor; and (c) determining whether the compound is an agonist or antagonist. The protein has at least 35% identity to an amino acid sequence selected from the group consisting of SEQUENCE ID NO 2, SEQUENCE ID NO 3, and fragments thereof.

The present invention further provides a method for determining whether a receptor binds to a TNF-gamma ligand. This method comprises (a) contacting a mammalian cell which expresses the TNF-gamma ligand with a receptor; (b) detecting the presence of the receptor; and (c) determining whether the receptor binds to the TNF-gamma ligand.

An antibody which specifically binds to at least one epitope encoded by TNF-gamma is provided herein. The antibody is polyclonal or monoclonal. The epitope comprises an amino acid sequence having at least 35% identity to an amino acid sequence selected from the group consisting of SEQUENCE ID NO 2, SEQUENCE ID NO 3 and fragments thereof.

Also provided is an assay kit for determining the presence of TNF-gamma antigen or antibody in a test sample, which comprises a container containing a TNF-gamma polypeptide having at least 35% identity to an amino acid sequence selected from the group consisting of SEQUENCE ID NO 2, SEQUENCE ID NO 3, and fragments thereof. Further, the polypeptide can be attached to a solid phase. In addition, the assay kit further comprises a container containing tools useful for collection of said sample selected from the group consisting lancets, absorbent paper, cloth, swabs and cups. Another assay kit for determining the presence of TNF-gamma antigen or antibody in a test sample which is provided by the present invention comprises a container containing an antibody which specifically binds to TNF-gamma antigen, wherein the antigen comprises at least one epitope of TNF-gamma having at least about 60% similarity to a sequence selected from the group consisting of SEQUENCE ID NO 2, SEQUENCE ID NO 3, and fragments thereof. Further, the assay kit comprises a container containing tools useful for collection of said sample selected from the group consisting lancets, absorbent paper, cloth, swabs and cups. Further, the antibody of the kit can be attached to a solid phase.

The present invention provides a method for producing a polypeptide comprising at least one epitope of TNF-gamma. The method comprises incubating host cells transformed with an expression vector, wherein the vector comprises a polynucleotide sequence encoding a polypeptide, which polypeptide comprises an amino acid sequence having at least 35% identity to an amino acid sequence selected from the group consisting of SEQUENCE ID NO 2, SEQUENCE ID NO 3, and fragments thereof.

The present invention further provides a method for detecting TNF-gamma antigen in a test sample suspected of containing the TNF-gamma antigen, comprising (a) contacting the test sample with an antibody or fragment thereof which specifically binds to at least one epitope of TNF-gamma antigen selected from the group consisting of SEQUENCE ID NO 2, SEQUENCE ID NO 3, and fragments thereof, for a time and under conditions sufficient for the formation of antibody/antigen complexes; (b) detecting said complexes. The method further comprises the antibody attached to a solid phase.

A method for detecting antibodies which bind to TNF-gamma antigen in a test sample suspected of containing the antibodies is provided by the invention. The method comprises (a) contacting said test sample with a TNF-gamma polypeptide, wherein the TNF-gamma polypeptide contains at least one TNF-gamma epitope comprising an amino acid sequence or fragment thereof having at least 35% identity to an amino acid sequence selected from the group consisting of SEQUENCE ID NO 2, SEQUENCE ID NO 3, and fragments thereof, for a time and under conditions sufficient to allow antigen/antibody complexes to form; and (b) detecting said complexes. The TNF-gamma polypeptide further can be attached to a solid phase.

Also provided by the present invention is a tissue culture grown cell comprising a nucleic acid sequence that encodes at least one epitope of TNF-gamma antigen or a fragment thereof, wherein the nucleic acid sequence is transfected into the cell and wherein the nucleic acid sequence is SEQUENCE ID NO 1 and fragments, analogs or complements thereof.

In addition, the present invention provides a method for producing antibodies which specifically bind to TNF-gamma antigen. The method comprises administering to an individual an isolated immunogenic polypeptide or fragment thereof, wherein the isolated immunogenic polypeptide comprises at least one TNF-gamma epitope and has at least 35% identity to a sequence selected from the group consisting of SEQUENCE ID NO 2, SEQUENCE ID NO 3, and fragments thereof, in an amount sufficient to produce an immune response. An addition method for producing antibodies which specifically bind to TNF-gamma antigen is provided, which comprises administering to a mammal a plasmid comprising a sequence which encodes at least one epitope of TNF-gamma, wherein the TNF-gamma sequence is selected from the group consisting of SEQUENCE ID NO 1 and fragments or complements thereof.

The present invention provides a composition of matter comprising a TNF-gamma polynucleotide or fragment thereof, wherein the polynucleotide has at least 50% identity to SEQUENCE ID NO 1 and fragments, analogs or complements thereof. Further provided is a composition of matter comprising a polypeptide containing at least one epitope encoded by TNF-gamma, wherein the polypeptide has at least 35% identity to a sequence selected from the group consisting of SEQUENCE ID NO 2, SEQUENCE ID NO 3 and fragments thereof. This polypeptide composition of matter further comprises a soluble fragment of the TNF-gamma protein and is capable of binding a receptor for TNF-gamma.

The present invention also provides a gene or fragment thereof which codes for TNF-gamma protein which comprises an amino acid sequence which has at least 35% identity to SEQUENCE ID NO 2. In addition, the present invention provides a gene or fragment thereof comprising DNA having at least 35% identity to SEQUENCE ID NO 1.

BRIEF DESCRIPTION OF THE DRAWINGS

FIG. 1 presents an amino acid alignment of TNF-gamma with several previously described members of the TNF family of ligands. hTNF-gamma is presented as SEQUENCE ID NO 2, hTNFa is presented as SEQUENCE ID NO 6, mTNFa is presented as SEQUENCE ID NO 7, hTNFb is presented as SEQUENCE ID NO 8, hLTb is presented as SEQUENCE ID NO 9 and hTRAIL is presented as SEQUENCE ID NO 10.

DETAILED DESCRIPTION OF THE INVENTION

A novel protein designated TNF-gamma is provided herein, along with the DNA that encodes the receptor binding domain of TNF-gamma, and recombinant vectors for producing TNF-gamma DNA.

The present invention also provides antibodies that specifically bind TNF-gamma proteins. In one embodiment, these antibodies are monoclonal antibodies.

Identification of a cDNA clone encoding human TNF-gamma is described in Example 1 below. The nucleotide sequence of the human TNF-gamma is presented in SEQUENCE ID NO 1, and the amino acid sequence is presented in SEQUENCE ID NO 2 and SEQUENCE ID NO 3.

The carboxyl-terminal ~150 amino acids of the members of the TNF family demonstrate sequence conservation. New members of the family therefore can be recognized by sequence homology to known family members in that region. The amino acid sequences disclosed herein reveal that TNF-gamma is a member of the TNF family of ligands. Smith et al, *Cell* 73:1349 (1993); Suda et. al. *Cell* 75:1169 (1993); Smith et. al. *Cell* 76:959 (1994). Of all known members of the TNF family, TNF-gamma is most closely related to TNF-alpha.

Conserved sequence located in the carboxyl terminal portion of the TNF family of ligands are identified in Smith et al *Cell*, supra. FIG. 1 presents an amino acid alignment of TNF-gamma (SEQUENCE ID NO 2) with several previously described members of the TNF family of ligands. Referring to FIG. 1, these are, from top to bottom, human TNF-gamma (SEQUENCE ID NO 2), human TNF-alpha (SEQUENCE ID NO 6), murine TNF-alpha (SEQUENCE ID NO 7), human TNF-beta (SEQUENCE ID NO 8), human Lymphotoxin (LT)-beta (SEQUENCE ID NO 9) and human TRAIL (SEQUENCE ID NO 10). Several highly conserved residues that are common to a majority of TNF family member are present in TNF-gamma. Amongst these residues are amino acids 119 (H), 138 (W), 147 (G), 160 (G), 162 (Y), 165 (Y), 166 (S), 167 (Q), 168 (V), 170 (F), 194 (L), 208 (Y), 212 (Y), 215 (G), 217 (F), 219 (L), 222 (G), 223 (D), 236 (L), 244 (L), and 246 (G).

Therapeutic Applications

Inflammation is a biological process whereby a region of the body is infiltrated by a variety of activated lymphocytes, in response to conditions such as bacterial infection or autoimmunity. While this process is beneficial, there are disease conditions caused by excessive and inappropriate inflammation which results in tissue damage. TNF has been implicated as a major cause of some of these conditions such as sepsis, rheumatoid arthritis and inflammatory bowel disease. Since TNF-gamma is closest to the TNF-alpha member of the TNF family, the present invention provides for the use of TNF-gamma an indicator of inflammation, and for blocking of TNF-gamma, by means such as anti-sense RNA, blocking antibody, or compounds developed by targeting TNF-gamma as a means to inhibit inflammation.

Programmed cell death (apoptosis) is a fundamental biological process whereby, given appropriate and external signals, cells are induced to self-destruction. This process had been described to occur during embrogenesis, endocrine-dependent tissue atrophy, normal tissue turnover, nervous and immune system development. In the case of the immune system, T-cells that recognize self epitopes are destroyed by apoptosis during maturation of T-cell in the thymus. It has been proposed that failure of self-reactive T-cells to undergo apoptosis is responsible for autoimmune disorders. Gammon et. al., *Immunology Today* 12:193 (1991. One characteristic of the TNF family is the ability of many family members to induce programmed cell death (apoptosis) in a variety of cells, both normal and of tumor origin (Wiley et al, *Immunity* 3:673–682, 1995, and references therein). Therefore, the present invention provides for use of TNF-gamma as an anti-cancer agent to induce apoptosis in cancer and tumor associated cells. The present invention also provides for use of TNF-gamma as an agent to eliminate inappropriate untransformed cells such as self-reactive T-cells. TNF-gamma may be internally administered alone or in conjunction with other agents or it may be used for the ex-vivo treatment and replacement of disease tissues. For instance circulating lymphoma cells may be exposed to immobilized TNF-gamma ex-vivo, and the treated blood reintroduced to the patient.

Another characteristic of the TNF family of ligands is to increase exposure of solid tumors to cells of the immune system by up-regulating vascular adhesion molecules, thereby attracting anti-tumor leukocytes to the region. M. W. Boehme, *Eur. J. Clin. Invest.*, supra. TNF also lowers the interstitial pressure of tumors, allowing concentrations of anti-cancer chemical agents or mixtures of anti-cancer chemical agents to enter the tumor in higher concentrations. The present invention provides for use a TNF-gamma as an adjunct to be used with anti-cancer chemotherapy agents for the treatment of tumors.

In addition, viral infection normal cells can make them susceptible to apoptosis induced by TNF family members, such as TNF-alpha and Fas Ligand. See, for example, C. V. Paya et. al., *J. Immunol.* 141:1989–1995 (1988); P. D. Katsiskas, *J. Exp. Med.* 181:2029–2036 (1995). The present invention provides for use a TNF-gamma as an anti-viral therapeutic agent, to be used alone or in conjunction with other agents, such as anti-viral compounds, or protein therapeutic agents. Since pre-treatment of virally infected cells with g-interferon has been shown to increase apoptosis induced by members of the TNF family, one embodiment of this application is to administer TNF-gamma together with other agents such as g-interferon.

This invention also provides for the use of TNF-gamma in developing any disorder mediated (directly or indirectly) by insufficient amounts or production of defective TNF-gamma protein. Purified human TNF-gamma protein may be administered to a patient with such a condition. Alternatively, gene therapy techniques for producing TNF-gamma peptide in vivo are also provided.

Pharmaceutical preparations of TNF-gamma comprise purified TNF-gamma and a physiologically acceptable carrier, diluent, or excipient. Such compositions include buffers, anti-oxidants, low molecular weight peptides, proteins, amino acids, carbohydrates, chelating agents, gluationone, and other excipients and stabilizers commonly found in pharmaceutical compositions.

The present invention provides methods for assaying a test sample for products of a TNF-gamma gene, which comprises making cDNA from mRNA in the test sample, and detecting the cDNA as an indication of the presence of the TNF-gamma gene. The method may include an amplification step, wherein portions of the cDNA corresponding to the gene or fragment thereof is amplified. Methods also are provided for assaying for the translation products of mRNAs. Test samples which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA; or as probes to determine the presence of certain cDNA sequences in test samples. Also disclosed are nucleic acid sequences which permit the production of encoded polypeptide sequences which are useful as standards or reagents in diagnostic immunoassays, targets for pharmaceutical screening assays and/or as components or target sites for various therapies. Monoclonal and polyclonal antibodies directed against at least one epitope contained within these polypeptide sequences are useful as delivery agents for therapeutic agents as well as for diagnostic tests for screening for diseases or conditions associated with the TNF-gamma gene provided herein, especially inflammation. Isolation of sequences of other portions of the gene of interest can be accomplished by utilizing probes or PCR primers derived from these nucleic acid sequences.

This allows additional probes of the mRNA or cDNA to be established, as well as corresponding encoded polypeptide sequences. These additional molecules are useful in the detecting, diagnosing, staging, monitoring, prognosticating, preventing or treating, or determining the predisposition to, diseases and conditions characterized by the TNF-gamma gene disclosed herein.

Techniques for determining the amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two amino acid sequences likewise can be compared by determining their "percent identity." The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

The compositions and methods described herein will enable the identification of certain markers as indicative of TNF-gamma disease; the information obtained therefrom will aid in the detecting, diagnosing, staging, monitoring, prognosticating, preventing or treating diseases or conditions associated with the TNF-gamma gene, especially inflammation, cancer, and graft-vs-host disease. Test methods include, for example, probe assays which utilize the sequence(s) provided herein and which also may utilize nucleic acid amplification methods such as the polymerase chain reaction (PCR), the ligase chain reaction (LCR); and hybridization. In addition, the nucleotide sequences provided herein contain open reading frames from which an immunogenic epitope may be found. This epitope is believed to be unique to the disease state or condition associated with the TNF-gamma gene. It also is thought that the TNF-gamma gene described herein is useful as a marker either elevated in disease such inflammation, altered in disease such as inflammation, or present as a normal protein but appearing in an inappropriate body compartment. The uniqueness of the epitope may be determined by (i) its immunological reactivity and specificity with antibodies directed against proteins and polypeptides encoded by the specific TNF-gamma gene and its non-reactivity or low degree of cross-reactivity, with other TNF markers. Methods for determining immunological reactivity are well-known and include but are not limited to, for example, radioimmunoassay (RIA), enzyme-linked immunosorbent assay (ELISA), hemagglutination (HA), fluorescence polarization immunoassay (FPIA); chemiluminescent immunoassay (CLIA), and others; several examples of suitable methods are described herein.

Unless otherwise stated, the following terms shall have the following meanings:

A polynucleotide "derived from" or "specific for" a designated sequence refers to a polynucleotide sequence which comprises a contiguous sequence of approximately at least about 6 nucleotides, is preferably at least about 8 nucleotides, is more preferably at least about 10–12 nucleotides, and even more preferably is at least about 15–20 nucleotides corresponding, i.e., identical to or complementary to, a region of the designated nucleotide sequence. The sequence may be complementary or identical to a sequence which is unique to a particular polynucleotide sequence as determined by techniques known in the art. Comparisons to sequences in databanks, for example, can be used as a method to determine the uniqueness of a designated sequence. Regions from which sequences may be derived include, but are not limited to, regions encoding specific epitopes, as well as non-translated and/or non-transcribed regions.

The derived polynucleotide will not necessarily be derived physically from the nucleotide sequence of interest under study, but may be generated in any manner, including but not limited to chemical synthesis, replication, reverse transcription or transcription, which is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified in ways known in the art to be consistent with an intended use.

A "fragment" of a specified polynucleotide refers to a polynucleotide sequence which comprises a contiguous sequence of approximately at least about 6 nucleotides, is preferably at least about 8 nucleotides, is more preferably at least about 10–12 nucleotides, and even more preferably is at least about 15–20 nucleotides corresponding, i.e., identical to or complementary to, a region of the designated nucleotide sequence.

The term "primer" denotes a specific oligonucleotide sequence complementary to a target nucleotide sequence and used to hybridize to the target nucleotide sequence. It serves as an initiation point for nucleotide polymerization catalyzed by either DNA polymerase, RNA polymerase or reverse transcriptase.

The term "probe" denotes a defined nucleic acid segment (or nucleotide analog segment, e.g., PNA as defined hereinbelow) which can be used to identify specific polynucleotide present in samples bearing the complementary sequence.

"Encoded by" refers to a nucleic acid sequence which codes for a polypeptide sequence, wherein the polypeptide sequence contains an amino acid sequence of at least 3 to 5 amino acids, more preferably at least 8 to 10 amino acids, and even more preferably at least 15 to 20 amino acids frp, a polypeptide encoded by the nucleic acid sequences. Also encompassed are polypeptide sequences which are immunologically identifiable with a polypeptide encoded by the sequence. Thus, a TNF-gamma "polypeptide," "protein," or "amino acid" sequence may have at least 60% similarity, preferably at least about 75% similarity, more preferably about 85% similarity, and most preferably about 95% similarity, to a polypeptide or amino acid sequence of TNF-gamma. This amino acid sequence can be selected from the group consisting of SEQUENCE ID NO: 2 and SEQUENCE ID NO: 3.

A "recombinant polypeptide" or "recombinant protein" or "polypeptide produced by recombinant techniques," which are used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide. The terms "polynucleotide," "oligomer," "oligonucleotide," and "oligo" are used interchangeably herein.

"A sequence corresponding to a cDNA" means that the sequence contains a polynucleotide sequence that is identical to or complementary to a sequence in the designated DNA. The degree (or "percent") of identity or complementarity to the cDNA will be approximately 50% or greater, will preferably be at least about 70% or greater, and more preferably will be at least about 90%. The sequence that corresponds to the identified cDNA will be at least about 50 nucleotides in length, will preferably be about 60 nucleotides in length, and more preferably, will be at least about 70 nucleotides in length. The correspondence between the gene or gene fragment of interest and the cDNA can be determined by methods known in the art, and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, i.e., contains less than about 50%, preferably less than about 70%, and more preferably, less than about 90% of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

"Purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and indicates a molecular chain of amino acids linked through covalent and/or noncovalent bonds. The terms do not refer to a specific length of the product. Thus, peptides, oligopeptides and proteins are included within the definition of polypeptide. The terms include post-expression modifications of the polypeptide, for example, glycosylations, acetylations, phosphorylations and the like. In addition, protein fragments, analogs, mutated or variant proteins, fusion proteins and the like are included within the meaning of polypeptide.

A "fragment" of a specified polypeptide refers to an amino acid sequence which comprises at least about 3–5 amino acids, more preferably at least about 8–10 amino acids, and even more preferably at least about 15–20 amino acids, derived from the specified polypeptide.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

"Purified product" refers to a preparation of the product which has been isolated from the cellular constituents with which the product is normally associated, and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

"Inflammation" or "inflammatory disease," as used herein, refer to infiltration of activated lymphocytes such as neutrophils, eosinophils, macrophages, T cells and B-cells, into a host tissue that results in damage to the host organism. Examples of inflammatory disease include but are not limited to conditions such as inflammatory bowel disease, sepsis, and rheumatoid arthritis.

An "Expressed Sequence Tag" or "EST" refers to the partial sequence of a cDNA insert which has been made by reverse transcription of mRNA extracted from a tissue, followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. "Specific binding member" as used herein means a member of a specific binding pair. That is, two different molecules where one of the molecules through chemical or physical means specifically binds to the second molecule. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazol or adamantane.

The various "signal-generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents

The present invention provides reagents such as polynucleotide sequences derived from a TNF-gamma of interest, polypeptides encoded therein, and antibodies developed from these polypeptides. The present invention also provides reagents such as oligonucleotide fragments derived from the disclosed polynucleotides and nucleic acid sequences complementary to the these polynucleotides. The polynucleotides or polypeptides or antibodies of the present invention may be used in the diagnosis, prognosis, and/or treatment of individuals with conditions associated with the TNF-gamma gene, such as inflammation, or to identify a predisposition to this condition. The sequences disclosed herein represent unique polynucleotides which can be used in assays or for producing a specific profile of gene transcription activity.

Selected TNF-gamma -derived polynucleotides can be used in the methods described herein for the detection of normal or altered gene expression. Such methods may employ the TNF-gamma derived polynucleotides disclosed herein or oligonucleotides, fragments or derivatives thereof, or nucleic acid sequences complementary to these polynucleotides.

The polynucleotides disclosed herein, their complementary sequences or fragments of either can be used in assays to detect, amplify or quantify genes, cDNAs or mRNAs relating to TNF-gamma disease and conditions associated with it. They also can be used to identify an entire or partial coding region which encodes for a TNF-gamma polypeptide. They further can be provided in individual containers in the form of a kit for assays, or provided as individual compositions. If provided in a kit for assays, other suitable reagents such as buffers, conjugates and the like may be included.

The polynucleotide(s) may be in the form of mRNA or DNA. Polynucleotides in the form of DNA, cDNA, genomic DNA, and synthetic DNA are within the scope of the present invention. The DNA may be double-stranded or single-stranded, and if single stranded may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and additional coding sequence such as a leader or secretory sequence or a proprotein sequence, or the coding sequence for the polypeptide (and optionally additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the form of the polypeptide. The polynucleotides may also encode for a proprotein which is the protein plus additional 5' amino acid residues. A protein having a prosequence is a proprotein and may in some cases be an inactive form of the protein. Once the prosequence is cleaved an active protein remains. Thus, the polynucleotide of the present invention may encode for a protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein. See, for example, I. Wilson et al., *Cell* 37:767 (1984).

It is contemplated that polynucleotides will be considered to hybridize to the sequences provided herein if there is at least 50%, and preferably at least 70%, identity between the polynucleotide and the sequence.

The present invention also provides an antibody produced by using a purified TNF-gamma gene polypeptide of which at least a portion of the polypeptide is encoded by the TNF-gamma gene polynucleotide selected from the polynucleotides provided herein. These antibodies may be used in the methods provided herein for the detection of TNF-gamma polypeptides in test samples. The antibody also may be used for therapeutic purposes, for example, in neutralizing the activity of a TNF-gamma polypeptide in conditions associated with altered or abnormal expression.

The present invention further relates to a TNF-gamma polypeptide which has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the TNF-gamma polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are preferably provided in an isolated form, and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Probes constructed according to the polynucleotide sequences of the present invention can be used in various assay methods to provide various types of analysis. For example, such probes can be used in Fluorescent In Situ Hybridization (FISH) technology to perform chromosomal analysis, and used to identify cancer-specific structural alterations in the chromosomes, such as deletions or translocations that are visible from chromosome spreads or detectable using PCR-generated and/or allele specific oligonucleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in fixed tissue specimens or cells.

This invention also provides teachings as to the production of the polynucleotides and polypeptides provided herein.

Probe Assays

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multigene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. No. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in European Patent No. 0320308B1 and European Patent No. 439182B1, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall et al., *PCR Methods and Applications* 4:80–84 (1994), which also is incorporated herein by reference.

Other known amplification methods which can be utilized herein include but are not limited to the so-called "NASBA" or "3SR" technique described in *PNAS USA* 87:1874–1878 (1990) (U.S. Pat. No. 5,290,905, issued Mar. 1, 1994) and also described in *Nature* 350 (No. 6313):91–92 (1991); Q-beta amplification as described in published European Patent Application (EPA) No. 4544610; strand displacement amplification (as described in G. T. Walker et al., *Clin. Chem.* 42:9–13 [1996]) and European Patent Application No. 684315; and target mediated amplification, as described by PCT Publication WO 9322461 (see U.S. Pat. 5,554,516 and U.S. Pat. No. 5,888,729).

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method herein provided are labeled with capture and detection labels wherein probes are labeled with one type of label and primers are labeled with the other type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences were cooled, the probe sequences preferentially bound the single stranded amplicon members. This finding is counterintuitive given that the probe sequences are generally selected to be shorter than the primer sequences and therefore have a lower melt temperature than the primers. Accordingly, the melt temperature of the amplicon produced by the primers should also have a higher melt temperature than the probes. Thus, as the mixture was cooled, the re-formation of the double stranded amplicon would be expected. As previously stated, however, this is not the case. The probes were found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugates presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

A test sample is typically anything suspected of containing a target sequence. Test samples can be prepared using methodologies well known in the art such as by obtaining a specimen from an individual and, if necessary, disrupting any cells contained therein to release target nucleic acids. Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well known amplification reactions that include thermal cycle reaction mixtures, particularly in PCR and GLCR. Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example, peptide nucleic acids which are disclosed in International Patent Application WO 92/20702 (equivalent to U.S. Pat. No. 5,714,331; issued Feb. 3, 1998) morpholino analogs which are described in U.S. Pat. Nos 5,185,444, 5,034,506, and 5,142,047; and the like. Depending upon the type of label carried by the probe, the probe is employed to capture or detect the amplicon generated by the amplification reaction. The probe is not involved in amplification of the target sequence and therefore may have to be rendered "non-extendible" in that additional dNTPs cannot be added to the probe. In and of themselves analogs usually are non-extendible and nucleic acid probes can be rendered non-extendible by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendible.

Accordingly, the ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1 are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. No. 625,566, filed Dec. 11, 1990 and Ser. No. 630,908, filed Dec. 20, 1990, which are each incorporated herein by reference, teach methods for labeling probes at their 5' and 3' termini, respectively. Publications WO92/10505, published Jun. 25, 1992 and WO 92/11388 published Jul. 9, 1992 teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., *Tet. Letters* 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' and 5' ends.

Capture labels are carried by the primers or probes and can be a specific binding member which forms a binding pair with the solid phase reagent's specific binding member. It will be understood, of course that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides wherein at least one polynucleotide is provided herein, hybridizing the test sample with the plurality of polynucleotides and detecting the hybridization complexes. The hybridization complexes are identified and quantitated to compile a profile which is indicative TNF-gamma disease. Expressed RNA sequences may further be detected by reverse transcription and amplification of the DNA product by procedures well-known in the art, including polymerase chain reaction (PCR).

Drug Screening and Gene Therapy

The present invention also encompasses the use of gene therapy methods for the introduction of anti-sense TNF-gamma gene derived molecules such as polynucleotides or oligonucleotides of the present invention into patients with conditions associated with abnormal expression of polynucleotides related to TNF-gamma disease including cancer. These molecules, including antisense RNA and DNA fragments and ribozymes, are designed to inhibit the translation of a TNF-gamma derived polynucleotide mRNA, and may be used therapeutically in the treatment of conditions associated with altered or abnormal expression of a TNF-gamma derived polynucleotide.

Alternatively, the oligonucleotides described above can be delivered to cells by procedures in the art such that the anti-sense RNA or DNA may be expressed in vivo to inhibit production of TNF-gamma derived polypeptide in the manner described above. Antisense constructs to TNF-gamma derived polynucleotide, therefore, reverse the action of TNF-gamma derived transcripts and may be used for treating TNF-gamma disease conditions, such as inflammation. These antisense constructs may also be used to treat tumor metastases.

Effects on tumor vasculature, such as those associated with this family of molecules (M. W. Boehme, *Eur. J. Clin. Invest.* 26: 404–410 1996), are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such proteins may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these proteins or genes which encode their expression may be useful in the prevention of metastases from the tumors described above either when used alone or in combination with radiotherapy and/or other chemotherapeutic agents.

Further uses include the treatment and prophylaxis of autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, i.e. keloids. Another use is as a birth control agent, by inhibiting ovulation and establishment of the placenta. TNF-gamma is also useful in the treatment of diseases that have angiogenesis as a pathologic consequence such as cat scratch disease (*Rochele minalia quintosa*) and ulcers (*Helicobacter pylori*).

TNF-gamma may be used in combination with other compositions and procedures for the treatment of diseases. For example, a tumor may be treated conventionally with surgery, radiation or chemotherapy combined with TNF-gamma, and then TNF-gamma may be subsequently administered to the patient to extend the dormancy of micrometastases and to stabilize and inhibit the growth of any residual primary tumor. Additionally, TNF-gamma, TNF-gamma fragments, TNF-gamma antisera, TNF-gamma receptor agonists, TNF-gamma receptor antagonists, or combinations thereof, may be combined with pharmaceutically acceptable excipients, and optionally sustained-release matrices, such as biodegradable polymers, to form therapeutic compositions.

A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Cytotoxic agents such as ricin, may be linked to TNF-gamma, and high affinity TNF-gamma peptide fragments, thereby providing a tool for destruction of cells that bind TNF-gamma. Peptides linked to cytotoxic agents may be infused in a manner designed to maximize delivery to the desired location. For example, ricin-linked high affinity TNF-gamma fragments may be delivered through a cannula into vessels supplying the target site or directly into the target. Such agents may also be delivered in a controlled manner through osmotic pumps coupled to infusion cannulae. A combination of TNF-gamma antagonists may be co-applied with stimulators of angiogenesis to increase vascularization of tissue. Therapeutic regimens of this type could provide an effective means of destroying metastatic cancer.

The present invention also encompasses gene therapy whereby the gene encoding TNF-gamma is regulated in a patient. Various methods of transferring or delivering DNA to cells for expression of the gene product protein, otherwise referred to as gene therapy, are disclosed in "Gene Transfer into Mammalian Somatic Cells in vivo", N. Yang, *Crit. Rev. Biotechn.* 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene which encodes a protein product that will treat the condition or that will make the tissue or organ more susceptible to a treatment regimen. As an example of a prophylactic strategy, a gene encoding TNF-gamma may be placed in a patient and thus prevent occurrence of angiogenesis; or a gene that makes tumor cells more susceptible to radiation could be inserted so that radiation of the tumor would cause increased killing of the tumor cells.

Many protocols for transfer of TNF-gamma DNA or TNF-gamma regulatory sequences are envisioned in this invention. Transfection of promoter sequences, other than one specifically associated with TNF-gamma, or other sequences which would increase production of TNF-gamma protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See *Genetic Engineering News*, Apr. 15, 1994. Such "genetic switches" could be used to activate TNF-gamma (or a TNF-gamma receptor) in cells not normally expressing these proteins.

Gene transfer methods for gene therapy fall into three broad categories: (1) physical (e.g., electroporation, direct gene transfer and particle bombardment), (2) chemical (e.g. lipid-based carriers and other non-viral vectors) and (3) biological (e.g. virus derived vectors). For example, non-viral vectors such as liposomes coated with DNA may be directly injected intravenously into the patient. It is believed that the liposome/DNA complexes are concentrated in the liver where they deliver the DNA to macrophages and Kupffer cells. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses. In vivo gene transfer involves introducing the DNA into the cells of the patient when the cells are within the patient. All three of the broad based categories described above may be used to achieve gene transfer in vivo, ex vivo, and in vitro.

Mechanical (i.e. physical) methods of DNA delivery can be achieved by direct injection of DNA, such as microinjection of DNA into germ or somatic cells, pneumatically delivered DNA-coated particles, such as the gold particles used in a "gene gun," and inorganic chemical approaches such as calcium phosphate transfection. It has been found that physical injection of plasmid DNA into muscle cells yields a high percentage of cells which are transfected and have a sustained expression of marker genes. The plasmid DNA may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer may also be employed for injecting DNA into cells, tissues and organs. With a particle bombardment device, or "gene gun," a motive force is generated to accelerate DNA-coated high density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art.

Chemical methods of gene therapy involve carrier mediated gene transfer through the use of fusogenic lipid vesicles such as liposomes or other vesicles for membrane fusion. A carrier harboring a DNA of interest can be conveniently introduced into body fluids or the bloodstream and then site specifically directed to the target organ or tissue in the body. Liposomes, for example, can be developed which are cell specific or organ specific. The foreign DNA carried by the liposome thus will be taken up by those specific cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

Transfected DNA may also be complexed with other kinds of carriers so that the DNA is carried to the recipient cell and then resides in the cytoplasm or in the nucleoplasm of the recipient cell. DNA can be coupled to carrier nuclear proteins in specifically engineered vesicle complexes and carried directly into the nucleus.

Carrier mediated gene transfer may also involve the use of lipid-based proteins which are not liposomes. For example, lipofectins and cytofectins are lipid-based positive ions that bind to negatively charged DNA, forming a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream; target cells that have the cell surface receptor will specifically bind the ligand and transport the ligand-DNA complex into the cell.

Biological gene therapy methodologies usually employ viral vectors to insert genes into cells. The term "vector" as used herein in the context of biological gene therapy means a carrier that can contain or associate with specific polynucleotide sequences and which functions to transport the specific polynucleotide sequences into a cell. The transfected cells may be cells derived from the patient's normal tissue, the patient's diseased tissue, or may be non-patient cells. Examples of vectors include plasmids and infective microorganisms such as viruses, or non-viral vectors such as the ligand-DNA conjugates, liposomes, and lipid-DNA complexes discussed above.

It may be desirable that a recombinant DNA molecule comprising a TNF-gamma DNA sequence is operatively linked to an expression control sequence to form an expression vector capable of expressing TNF-gamma. Alternatively, gene regulation of TNF-gamma may be accomplished by administering proteins that bind to the TNF-gamma gene, or control regions associated with the TNF-gamma gene, or its corresponding RNA transcript to modify the rate of transcription or translation.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome. For example, altered retrovirus vectors have been used in ex vivo methods to introduce genes into peripheral and tumor-infiltrating lymphocytes, hepatocytes, epidermal cells, myocytes, or other somatic cells (which may then introduced into the patient to provide the gene product from the inserted DNA).

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

When used in the above or other treatments, a therapeutically effective amount of one of the proteins of the present invention may be employed in pure form or, where such forms exist, in pharmaceutically acceptable salt form. By a "therapeutically effective amount" of the protein of the invention is meant a sufficient amount of the protein to treat an angiogenic disease, (for example, to limit tumor growth or to slow or block tumor metastasis) at a reasonable benefit/risk ratio applicable to any medical treatment. It will be understood, however, that the total daily usage of the proteins and compositions of the present invention will be decided by the attending physician within the scope of sound medical judgment. The specific therapeutically effective dose level for any particular patient will depend upon a variety of factors including the disorder being treated and the severity of the disorder; activity of the specific protein employed; the specific composition employed, the age, body weight, general health, sex and diet of the patient; the time of administration, route of administration, and rate of excretion of the specific protein employed; the duration of the treatment; drugs used in combination or coincidential with the specific protein employed; and like factors well known in the medical arts. For example, it is well within the skill of the art to start doses of the protein at levels lower than those required to achieve the desired therapeutic effect and to gradually increase the dosage until the desired effect is achieved.

The proteins of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxy-ethansulfonate (isethionate), lactate, maleate, methanesulfonate, nicotinate, 2-naphthalenesulfonate, oxalate, pamoate, pectinate, persulfate, 3-phenylpropionate, prcrate, pivalate, propionate, succinate, tartrate, thiocyanate, phosphate, glutamate, bicarbonate, p-toluenesulfonate and undecanoate. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium or magnesium or with organic basis. Preferred salts of the proteins of the invention include phosphate, tris and acetate.

The total daily dose of the proteins of this invention administered to a human or lower animal may range from about 0.0001 to about 1 mg/kg of a patient's body mass/day. If desired, the effective daily dose may be divided into multiple doses for purposes of administration; consequently, single dose compositions may contain such amounts or submultiples thereof to make up the daily dose.

Alternatively, a protein of the present invention may be administered as pharmaceutical compositions containing the protein of interest in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions may be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Injectable depot forms are made by forming microencapsule matrices of the drug in biodegradable polymers such as polylactide-polyglycolide, poly(orthoesters) and poly (anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues.

The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent, such as a liquid or solid non-ionic surface active agent or may be a solid anionic surface active agent. It is preferred to use the solid anionic surface active agent in the form of a sodium salt.

A further form of topical administration is to the eye. A protein of the invention is delivered in a pharmaceutically acceptable ophthalmic vehicle, such that the protein is maintained in contact with the ocular surface for a sufficient time period to allow the protein to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically-acceptable ophthalmic vehicle may, for example, be an ointment, vegetable oil or an encapsulating material. alternatively, the a protein of the invention may be injected directly into the vitrious and aqueous humour.

Compositions for rectal or vaginal administration are preferably suppositories which may be prepared by mixing the proteins of this invention with suitable non-irritating excipients or carriers such as cocoa butter, polyethylene glycol or a suppository wax which are solid at room temperature but liquid at body temperature and therefore melt in the rectum or vaginal cavity and release the active protein.

Proteins of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a protein of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

While the proteins of the invention can be administered as the sole active pharmaceutical agent, they may also be used in combination with one or more agents which are conventionally administered to patients for treating angiogenic diseases. For example, when used in the treatment of solid tumors, proteins of the invention may be administered with anti-neoplastic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like.

Total daily dose of TNF-gamma (administered in combination with a protein of this invention) to be administered to a human or other mammal host in single or divided doses may be in amounts, for example, from 0.0001 to 300 mg/kg body weight daily and more usually 1 to 300 mg/kg body weight.

It will be understood that agents which can be combined with the protein of the present invention for the inhibition, treatment or prophylaxis of angiogenic diseases are not limited to those listed above, but include in principle any agents useful for the treatment or prophylaxis of angiogenic diseases.

Synthetic peptide fragments of TNF-gamma may also be produced and used in a variety of applications. As examples, different peptide fragments of TNF-gamma can be used (1) as agonists and antagonists active at TNF-gamma binding sites, (2) as a means to isolate a TNF-gamma receptor, (3) as antigens for the development of specific antisera, (4) as peptides for use in diagnostic kits and (5) as peptides linked to or used in combination with cytotoxic agents (for targeted killing of cells that bind TNF-gamma. The amino acid sequences that comprise these peptides may be selected on the basis of their position on the exterior regions of the molecule which are accessible for binding to antisera. Furthermore, these peptide sequences may be compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules, thereby enhancing the potential for high specificity in the development of antisera, agonists and antagonists to TNF-gamma.

Systematic substitution of amino acids within these synthesized peptides may yield high affinity peptide agonists and antagonists to the TNF-gamma receptor that enhance or diminish TNF-gamma binding to its receptor. Such agonists may be used to suppress the growth of micrometastases, thereby limiting the spread of cancer. In cases of inadequate vascularization, antagonists to TNF-gamma may be applied to block the inhibitory effects of TNF-gamma and promote angiogenesis. For example, this type of treatment may have therapeutic effects in promoting wound healing in diabetics.

TNF-gamma peptides may also be employed to develop affinity columns for isolation of a TNF-gamma receptor in for example, cultured endothelial cells. As is known in the art, isolation and purification of a TNF-gamma receptor may be followed by amino acid sequencing to identify and isolate polynucleotides which encode the TNF-gamma receptor. Such polynucleotides may then be cloned into a suitable expression vector and transfected into tumor cells. Expression of the receptor by the transfected tumor cells would enhance the responsiveness of these cells to endogenous or exogenous TNF-gamma, thereby decreasing the rate of metastatic growth. Furthermore, recombinant expression of this receptor would allow greater amounts of receptor to be produced, e.g. to produce a sufficient quantity for use in high throughput screening assays to identify smaller antagonists which mimic the action of TNF-gamma.

TNF-gamma peptides of the present invention can also be used as antigens generate polyclonal or monoclonal antibodies that are specific for the TNF-gamma inhibitor. One way in which such antibodies could be used is in diagnostic methods and kits to detect or quantify TNF-gamma in a body fluid or tissue. Results from these tests could be used to diagnose or determine the prognostic relevance of TNF-gamma.

TNF-gamma peptides may be chemically coupled to isotopes, enzymes, carrier proteins, cytotoxic agents, fluorescent molecules, chemiluminescent, bioluminescent and other proteins for a variety of applications. For example, a TNF-gamma polypeptide may be labeled to facilitate testing of its ability to bind TNF-gamma antisera or to detect cell types which possess a TNF-gamma receptor. The coupling technique is generally chosen on the basis of the functional groups available on the amino acids of the TNF-gamma sequence including, but not limited to amino, sulfhydral, carboxyl, amide, phenol, and imidazole. Various reagents used to effect such couplings include among others, glutaraldehyde, diazodzed benzidine, carbodiimide, and p-benzoquinone.

The efficiency of the coupling reaction is determined using different techniques appropriate for the specific reaction. For example, radiolabeling of a TNF-gamma peptide with $I^{125}$ may be accomplished using chloramine T and $NaI^{125}$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, a labeled TNF-gamma peptide may be obtained which is free from unreacted $NaI^{125}$.

Another application of peptide conjugation is for production of polyclonal antisera. For example, TNF-gamma peptides containing lysine residues may be linked to purified bovine serum albumin using glutaraldehyde. The efficiency of this reaction may be determined by measuring the incorporation of radiolabeled peptide. Unreacted glutaraldehyde and peptide may be separated by dialysis and the conjugate stored for subsequent use.

The production of antiserum against TNF-gamma, TNF-gamma analogs, peptide fragments of TNF-gamma and the TNF-gamma receptor can be performed using established techniques known to those skilled in the art. For example, polyclonal antisera may be raised in rabbits, sheep, goats or other animals. TNF-gamma peptides conjugated to a carrier molecule such as bovine serum albumin, or TNF-gamma itself, may be combined with an adjuvant mixture, emulsified and injected subcutaneously at multiple sites on the back, neck, flanks, and sometimes in the footpads of a suitable host. Generally, booster injections are then given at regular intervals, such as every 2 to 4 weeks. Approximately 7 to 10 days after each injection, blood samples are obtained by venipuncture, using, for example, the marginal ear veins after dilation. The blood samples are allowed to clot overnight at 4° C. and are centrifuged at approximately 2400×g at 4° C. for about 30 minutes. The serum is removed, aliquoted, and stored at 4° C. for immediate use or at −20 to −90° C. for subsequent analysis.

Serum samples from generation of polyclonal antisera or media samples from production of monoclonal antisera may be analyzed for determination of antibody titer and in particular, for the determination of high titer antisera. Subsequently, the highest titer TNF-gamma antisera may be tested to establish the following; a) optimal antiserum dilution for highest specific binding of the antigen and lowest non-specific binding, b) ability to bind increasing amounts of TNF-gamma peptide in a standard displacement curve, c) potential cross-reactivity with related peptides and proteins, including plasminogen and also TNF-gamma of related species, and d) ability to detect TNF-gamma peptides in extracts of plasma, urine, tissues, and in cell culture media.

Titer may be established through several means known in the art, such as by dot blot and density analysis, and also by precipitation of radiolabeled peptide-antibody complexes using protein A, secondary antisera, cold ethanol or charcoal-dextran followed by activity measurement with a gamma counter. If desired, the highest titer antisera may be purified on affinity columns. For example, TNF-gamma peptides may be coupled to a commercially available resin and used to form an affinity column. Antiserum samples may then be passed through the column so that TNF-gamma antibodies bind (via TNF-gamma) to the column. These bound antibodies are subsequently eluted, collected and evaluated for determination of titer and specificity.

The present invention also provides a method of screening a plurality of compounds for specific binding to a TNF-gamma derived polypeptide, or any fragment thereof, to identify at least one compound which specifically binds the TNF-gamma derived polypeptide. Such a method comprises the steps of providing at least one compound; combining the TNF-gamma derived polypeptide with each compound under suitable conditions for a time sufficient to allow binding; and detecting TNF-gamma polypeptide binding to each compound.

Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of the TNF-gamma derived polypeptide. For triple helix, see, for example, Lee et al, *Nucl. Acids Res.* 6:3073 (1979); Cooney et al, *Science* 241:456 (1988); and Dervan et al, *Science* 251:1360 (1991). The antisense RNA oligonucleotide hybridizes to the mRNA in vivo and blocks translation of an mRNA molecule into the TNF-gamma derived polypeptide. For antisense, see, for example, Okano, *J. Neurochem.* 56:560 (1991); and "Oligodeoxynucleotides as Antisense Inhibitors of Gene Expression", CRC Press, Boca Raton, Fla. (1988). Antisense oligonucleotides act with greater efficacy when modified to contain artificial internucleotide linkages which render the molecule resistant to nucleolytic cleavage. Such artificial internucleotide linkages include but are not limited to methylphosphonate, phosphorothiolate and phosphoroamydate internucleotide linkages.

The polypeptide or peptide fragment employed in such a test may either be free in solution, affixed to a solid support, borne on a cell surface or located intracellularly. One method of drug screening utilizes eukaryotic or prokaryotic host cells which are stably transformed with recombinant nucleic acids which can express the polypeptide or peptide fragment. Drugs may be screened against such transformed cells in competitive binding assays. For example, the formation of complexes between a polypeptide and the agent being tested can be measured in either viable or fixed cells.

The present invention thus provides methods of screening for drugs or any other agent which can be used to treat diseases associated with the TNF-gamma gene by measuring the effect of the drug on the amount of TNF-gamma nucleotide or protein produced or biological effects of TNF-gamma. Examples of these types of measurements include but are not limited to measuring $Ca^{++}$ efflux, cAMP production, aptopsis, etc. These measurements are known to those of ordinary skill in the art. The present invention also provides for measuring the effect of the drug on a recombinant reporter gene designed to respond to TNF-gamma. These methods comprise measuring the effect of applying the drug to a natural or genetically engineered experimental organism, such as cultured cells, bacteria, or laboratory animal and measuring the amount of TNF-gamma nucleotide or protein produced, or biological effects of TNF gamma, or quantity of a recombinant reporter gene such as luciferase.

The present invention thus provides methods of screening for drugs or any other agent which can be used to treat diseases associated with the TNF-gamma gene. These methods comprise contacting the drug with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is a measure of the ability of the particular drug to bind to polypeptide or to interfere with the polypeptide/cell complex.

The present invention also encompasses the use of competitive drug screening assays in which neutralizing antibodies capable of binding polypeptide specifically compete with a test drug for binding to the polypeptide or fragment thereof. In this manner, the antibodies can be used to detect the presence of any polypeptide in the test sample which shares one or more antigenic determinants with a polypeptide provided herein.

Another technique for drug screening provides high throughput screening for compounds having suitable binding affinity to at least one polypeptide disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well-known in the art. Purified polypeptide can also be coated directly onto plates for use in the drug screening techniques described herein. In addition, non-neutralizing antibodies can be used to capture the polypeptide and immobilize it on the solid support. See, for example, European Patent No. 0003564B1, which is incorporated herein by reference The goal of rational drug design is to produce structural analogs of biologically active polypeptides of interest or of the small molecules including agonists, antagonists, or inhibitors with which they interact. Such structural analogs can be used to fashion drugs which are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors.

Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J Biochem.* (Tokyo) 113 (6):742–746 (1993), incorporated herein by reference.

It also is possible to isolate a target-specific antibody, selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then could be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which are derivable from the nucleic acid sequence provided herein will provide guidance to those employing computer modeling techniques in place of or in addition to x-ray crystallography.

Antibodies specific to the TNF-gamma derived polypeptide may further be used to inhibit the biological action of the polypeptide by binding to the polypeptide. In this manner, the antibodies may be used in therapy, for example, to treat TNF-gamma diseases including inflammation.

Further, such antibodies can detect the presence or absence of TNF-gamma derived polypeptide and, therefore, are useful as diagnostic markers for the diagnosis of TNF-gamma disease, especially inflammation. Such antibodies may also function as a diagnostic marker for TNF-gamma disease conditions such as inflammation. The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function. The antagonist, for example, could be an antibody against the polypeptide which eliminates the activity of TNF-gamma derived polypeptide by binding to TNF-gamma derived polypeptide, or in some cases the antagonist may be an oligonucleotide. Examples of small molecule inhibitors include but are not limited to small peptides or peptide-like molecules.

The antagonists and inhibitors may be employed as a composition with a pharmaceutically acceptable carrier, including but not limited to saline, buffered saline, dextrose, water, glycerol, ethanol and combinations thereof. Administration of TNF-gamma derived polypeptide inhibitors are preferably systemic. The present invention also provides an antibody which inhibits the action of such polypeptide.

Recombinant Technology

The present invention provides host cells and expression vectors comprising polynucleotides of the present invention and methods for the production of polypeptides they encode. Such methods comprise culturing the host cells under conditions suitable for the expression of the TNF-gamma derived polynucleotide and recovering the TNF-gamma derived polypeptide from the cell culture.

The present invention also provides vectors which include polynucleotides of the present invention, host cells which are genetically engineered with vectors of the present invention and the production of polypeptides of the present invention by recombinant techniques.

Host cells are genetically engineered (transduced or transformed or transfected) with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants or amplifying TNF-gamma derived genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include but are not limited to LTR or SV40 promoter, the E. coli lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as E. coli, Salmonella typhimurium; Streptomyces sp.; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above.

The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Plasmid pINCY is generally identical to the plasmid pSPORT1 (available from Life Technologies, Gaithersburg, Md.) with the exception that it has two modifications in the polylinker (multiple cloning site). These modifications are (1) it lacks a HindIII restriction site and (2) its EcoRI restriction site lies at a different location. pINCY is created from pSPORT1 by cleaving pSPORT1 with both HindIII and EcoR1 and replacing the excised fragment of the polylinker with synthetic DNA fragments SEQUENCE ID NO 11 and SEQUENCE ID NO 12. This replacement may be made in any manner known to those of ordinary skill in the art. For example, the two nucleotide sequences SEQUENCE ID NO 11 and SEQUENCE ID NO 12 may be generated synthetically with 5' terminal phosphates, mixed together and then ligated under standard conditions for performing staggered end ligations into the pSPORT1 plasmid cut with HindIII and EcoR1. Suitable host cells (such as E. coli DH5$\mu$ cells) then are transformed with the ligated DNA and recombinant clones are selected for ampicillin resistance. Plasmid DNA then is prepared from individual clones and subjected to restriction enzyme analysis or DNA sequencing in order to confirm the presence of insert sequences in the proper orientation. Other cloning strategies known to the ordinary artisan also may be employed.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retrovirus, and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology", 2nd edition, Appleton and Lang, Paramount Publishing, East Norwalk, Conn. (1994).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, (Cold Spring Harbor, N.Y., 1989), which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan.

Various mammalian cell culture systems can also be employed to express recombinant protein. Examples of mammalian expression systems include the COS-7 lines of monkey kidney fibroblasts described by Gluzman, Cell 23:175 (1981), and other cell lines capable of expressing a compatible vector, such as the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

The TNF-gamma polypeptide is recovered and purified from recombinant cell cultures by known methods including ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price et al., J. Biol. Chem. 244:917 [1969]). Protein refolding steps can be used, as necessary, in completing configuration of the protein. Finally, high performance liquid chromatography (HPLC) can be employed for final purification steps.

The polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The present invention further includes modified versions of the TNF-gamma polypeptide to preclude glycosylation while allowing expression of a reduce carbohydrate form of the protein in yeast, insect or mammalian expression systems. Known methods for inactivating glycosylation sites include, but are not limited to, those presented in U.S. Pat. No. 5,071,972 and EP 276,846, which are incorporated herein by reference.

Other variants included in the present invention include removal of sequences encoding cystein residues, thereby preventing formation of incorrect intramolecular disulfide bridges which decrease biological activity of the protein product. The present invention also includes removal of site of proteolytic processing, allowing expression in system which contain the problematic protease, for example the KEX2 protease in yeast. Known methods for removing such protease sites include but are not limited to one method for removing KEX2 sites presented in EP212,914.

The present invention includes TNF-gamma peptides in the form of oligomers, dimers, trimers and higher order oligomers. Oligomers may be formed by several means including but not limited to disulfide bonds between peptides, non-covalent interactions between peptides, and poly-ethylene-glycol linkages between peptides.

The fusion of TNF-gamma peptides to peptide linkers or peptides that are capable of promoting oligomers is also encompassed in this invention. Such peptides include but are not limited to leucine zippers and antibody derived peptides, such as is described in Landschulz et al., Science 240:1759 (1988); Hollenbaugh and Aruffo, "Construction of Immunoglobin Fusion Proteins", in Current Protocols in Immunology Supplement 4, pgs 10.19.1–10.19.11 (1992) John Wiley and sons, New York, N.Y.

The starting plasmids can be constructed from available plasmids in accord with published, known procedures. In addition, equivalent plasmids to those described are known in the art and will be apparent to the ordinarily skilled artisan.

The following is the general procedure for the isolation and analysis of cDNA clones. In a particular embodiment disclosed herein, mRNA was isolated from TNF-gamma and used to generate the cDNA library. TNF-gamma was obtained from synovium of patients with rheumatoid arthritis by surgical extraction.

A cDNA insert from an isolate of TNF-gamma was sequenced in its entirety, analyzed in detail set forth in the Examples and is disclosed in the Sequence Listing as SEQUENCE ID NO 1. These polynucleotides encode a sufficient portion of the gene of interest to encode a biologically active molecule. The lack of full length clones is attributed to the fact that many genes are several hundred, and sometimes several thousand, bases in length and, with current technology, cannot be cloned in their entirety because of vector limitations, incomplete reverse transcription of the first strand, or incomplete replication of the second strand. Contiguous, secondary clones containing additional nucleotide sequence may be obtained using a variety of methods known to those of skill in the art.

Methods for DNA sequencing are well known in the art. Conventional enzymatic methods employ DNA polymerase, Klenow fragment, Sequenase (U.S. Biochemical Corp., Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while the other two reading frames tend to contain numerous stop codons. In such cases reading frame determination is straightforward. In other more difficult cases, further analysis is required. Ultimate confirmation of a correct open reading frame is achieved by using the nucleotide sequence to produce a biologically active molecule, by such methods that are familiar to those of skill in the art.

Algorithms have been created to analyze the occurrence of individual nucleotide bases at each putative codon triplet. See, for example J. W. Fickett, Nuc. Acids Res. 10:5303 (1982). Coding DNA for particular organisms (bacteria, plants, and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well established recombinant DNA techniques. See J. Sambrook et al., supra. Vectors of interest include cloning vectors, such as plasmids, cosmids, phage derivatives, phagemids, as well as sequencing, replication, and expression vectors, and the like. In general, such vectors contain an origin of replication functional in at least one organism, convenient restriction endonuclease digestion sites, and selectable markers appropriate for particular host cells. The vectors can be transferred by a variety of means known to those of skill in the art into suitable host cells which then produce the desired DNA, RNA or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel et al., Current Protocols in Molecular Biology, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and as such may contain unidentified nucleotides. These will not present a problem to those skilled in the art who wish to practice the invention. Several methods employing standard recombinant techniques, described in J. Sambrook et al., supra, or periodic updates thereof, may be used to complete the missing sequence information. The same techniques used for obtaining a full length sequence, as described herein, may be used to obtain nucleotide sequence.

Expression of a particular cDNA may be accomplished by subcloning the cDNA into an appropriate expression vector and transfecting this vector into an appropriate expression host. The cloning vector used for the generation of the TNF-gamma cDNA library can be used for transcribing mRNA of a particular cDNA. Immediately following these eight residues is an engineered bacteriophage promoter useful for artificial priming and transcription and a number of unique restriction sites, including EcoR I, for cloning. The vector can be transfected into an appropriate host strain of E. coli.

Induction of the isolated bacterial strain with isopropylthiogalactoside (IPTG) using standard methods will produce a fusion protein which contains the first seven residues of beta-galactosidase, about 15 residues of linker, and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require the addition of 3' poly A tail if the sequence of interest lacks poly A, and/or the addition of a intron sequence which promotes proper splicing and processing of the mRNA, but does not alter the amino acid sequence of the gene product.

Further this invention encompasses expression vector whereby secretion of the protein outside of the host cell is achieved by fusing in frame DNA encoding signal peptide sequences to the open reading frame encoding TNF-gamma. These sequence may be prokaryotic, eukaryotic, or viral in origin.

Additionally, the vector may contain promoters or enhancers which increase gene expression. Such promoters are host specific and include but are not limited to MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays

The polypeptides including their fragments or derivatives or analogs thereof of the present invention, or cells expressing them, can be in a variety of assays, many of which are described herein, for the detection of antibodies to TNF-gamma. They also can be used as an immunogen to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide corresponding to a sequence of the present invention can be obtained by direct injection of the polypeptide into an animal or by administering the polypeptide to an animal such as a mouse, rabbit, goat or human. A mouse, rabbit or goat is preferred. The antibody so obtained then will bind the polypeptide itself. In this manner, even a sequence encoding only a fragment of the polypeptide can be used to generate antibodies that bind the native polypeptide. Such antibodies can then be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256:495–497 (1975), the trioma technique, the human B-cell hybridoma technique as described by Kozbor et al, *Immun. Today* 4:72 (1983), and the EBV-hybridoma technique to produce human monoclonal antibodies as described by Cole et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the monoclonal antibodies or fragment thereof of the present invention can be employed in various assay systems to determine the presence, if any, of TNF-gamma derived polypeptide in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of a TNF-gamma derived polypeptide antigen present in the test sample and captured on the solid phase, if any, is determined by detecting the measurable signal generated by the signal generating compound. The amount of TNF-gamma derived polypeptide antigen present in the test sample is proportional to the signal generated.

Or, a polyclonal or monoclonal TNF-gamma-derived polypeptide antibody or fragment thereof, or a combination of these antibodies which is bound to a solid support, the test sample and an indicator reagent comprising a monoclonal or polyclonal antibody or fragments thereof, which specifically binds to TNF-gamma derived polypeptide antigen, or a combination of these antibodies to which a signal generating compound is attached, are contacted to form a mixture. This mixture is incubated for a time and under conditions sufficient to form antibody/antigen/antibody complexes. The presence, if any, of TNF-gamma derived polypeptide present in the test sample and captured on the solid phase is determined by detecting the measurable signal generated by the signal generating compound. The amount of TNF-gamma derived polypeptide proteins present in the test sample is proportional to the signal generated.

In another assay format, one or a combination of at least two monoclonal antibodies of the invention can be employed as a competitive probe for the detection of antibodies to TNF-gamma derived polypeptide protein. For example, TNF-gamma derived polypeptide proteins such as the recombinant antigens disclosed herein, either alone or in combination, are coated on a solid phase. A test sample suspected of containing antibody to TNF-gamma derived polypeptide antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of TNF-gamma derived polypeptide antigens in fixed tissue sections, as well as fixed cells by immunohistochemical analysis. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific TNF-gamma derived polypeptide proteins from cell cultures or biological tissues such as to purify recombinant and native TNF-gamma derived polypeptide antigens and proteins.

The monoclonal antibodies of the invention can also be used for the generation of chimeric antibodies for therapeutic use, or other similar applications.

The monoclonal antibodies or fragments thereof can be provided individually to detect TNF-gamma derived polypeptide antigens. Combinations of the monoclonal antibodies (and fragments thereof) provided herein also may be used together as components in a mixture or "cocktail" of at least one TNF-gamma derived polypeptide antibody of the invention with antibodies to other TNF-gamma derived polypeptide regions, each having different binding specificities. Thus, this cocktail can include the monoclonal antibodies of the invention which are directed to TNF-gamma derived polypeptide proteins of TNF-gamma and other monoclonal antibodies to other antigenic determinants of TNF-gamma derived polypeptide genome.

The polyclonal antibody or fragment thereof which can be used in the assay formats should specifically bind to a TNF-gamma derived polypeptide region or other TNF-gamma derived polypeptide proteins used in the assay. The polyclonal antibody used preferably is of mammalian origin; human, goat, rabbit or sheep anti-TNF-gamma derived polypeptide polyclonal antibody can be used. Most preferably, the polyclonal antibody is rabbit polyclonal anti-TNF-gamma derived polypeptide antibody. The polyclonal antibodies used in the assays can be used either alone or as a cocktail of polyclonal antibodies. Since the cocktails used in the assay formats are comprised of either monoclonal antibodies or polyclonal antibodies having different TNF-gamma derived polypeptide specificity, they would be useful for diagnosis, evaluation and prognosis of TNF-gamma derived polypeptide condition, as well as for studying TNF-gamma derived polypeptide protein differentiation and specificity.

It is contemplated and within the scope of the present invention that the TNF-gamma derived polypeptide may be detectable in assays by use of a recombinant antigen as well as by use of a synthetic peptide or purified peptide, which contains an amino acid sequence of TNF-gamma derived polypeptide. It also is within the scope of the present invention that different synthetic, recombinant or purified peptides identifying different epitopes of the TNF-gamma derived polypeptide can be used in combination in an assay to diagnose, evaluate, or prognosticate the TNF-gamma disease condition. In this case, these peptides can be coated onto one solid phase, or each separate peptide may be coated on separate solid phases, such as microparticles, and then combined to form a mixture of peptides which can be later used in assays. Furthermore, it is contemplated that multiple peptides which define epitopes from different polypeptides may be used in combination to make a diagnosis, evaluation, or prognosis of TNF-gamma disease. Peptides coated on solid phases or labeled with detectable labels are then allowed to compete with peptides from a patient sample for a limited amount of antibody. A reduction in binding of the synthetic, recombinant, or purified peptides to the antibody (or antibodies) is an indication of the presence of TNF-gamma-secreted polypeptides in the patient sample which in turn indicates the presence of TNF-gamma gene in the patient. Such variations of assay formats are known to those of ordinary skill in the art and are discussed herein below.

In another assay format, the presence of antibody and/or antigen to TNF-gamma derived polypeptide can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from human expression systems may be utilized as well as monoclonal antibodies produced from the proteins derived from the mammalian expression systems as disclosed herein. Such assay systems are described in greater detail in EP Publication No. 0473065.

In yet other assay formats, the polypeptides disclosed herein may be utilized to detect the presence of anti-TNF-gamma derived polypeptide in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of TNF-gamma derived polypeptide antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as *E. coli* is used as a capture antigen on a solid phase, a test sample is added to the so-prepared solid phase, and a recombinant protein derived from a different source (i.e., non-*E. coli*) is utilized as a part of an indicator reagent. Likewise, combinations of a recombinant antigen on a solid phase and synthetic peptide in the indicator phase also are possible. Any assay format which utilizes an antigen specific for TNF-gamma derived polypeptide from a first source as the capture antigen and an antigen specific for TNF-gamma derived polypeptide from a different second source are contemplated. Thus, various combinations of recombinant antigens, as well as the use of synthetic peptides, purified proteins, and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in European Patent No. 273115B1.

Also, the methods of the present invention can be adapted for use in systems which utilize microparticle technology including in automated and semi-automated systems wherein the solid phase comprises a microparticle (magnetic or non-magnetic). Such systems include those described in European Patent No. 0425633B1 and European Patent No. 0424634B1, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (either recombinant or synthetic) employed in the assay. Other components such as buffers, controls, and the like, known to those of ordinary skill in art, may be included in such test kits. It also is contemplated to provide test kits which have means for collecting test samples comprising accessible body fluids, e.g. blood, urine, saliva, and stool. Such tools useful for collection ("collection materials") include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization, and preservation of test specimens obtained by surgery or needle biopsy are also useful. It is contemplated that all kits may be configured in two components which can be provided separately; one component for collection and transport of the specimen, and the other component for the analysis of the specimen. The collection component, for example, can be provided to the open market user while the components for analysis can be provided to others such as laboratory personnel for determination of the presence, absence or amount of analyte. Further, kits for the collection, stabilization, and preservation of test specimens may be configured for use by untrained personnel and may be available in the open market for use at home with subsequent transportation to a laboratory for analysis of the test sample.

Clone 1235095 was accorded A.T.C.C. Deposit No. 98184 and was deposited with the American Type Culture Collection, 10801 University Boulevard, Manassas, Va. 20110-2209 on Sep. 26, 1996.

The present invention will now be described by way of examples, which are meant to illustrate, but not to limit, the scope of the present invention.

EXAMPLES

Example 1

Identification of TNF-Gamma Library EST Clones

A. Library Comparison of Expressed Sequence Tags (ESTs) or Transcript Images. Partial sequences of cDNA clone inserts, so-called expressed sequence tags (ESTs), were derived from cDNA libraries made from numerous tissues, both diseased and normal, and entered into a database (LIFESEQ™ database, available from Incyte Pharmaceuticals, Palo Alto, Calif.) as gene transcript images. The sequences then were evaluated to identify EST sequences whose predicted amino acid sequences were representative the TNF family of genes. Once such an EST was identified, the known sequence of the gene represented by the EST was expanded by searching all available human DNA sequence databases, both publicly and privately, available for overlapping sequences with significant homology. This expanded sequence will from here on be described as the contig. Having done this, the 5' end furthest extending clone available at the time was obtained from the EST provider (Incyte Pharmaceuticals), and the sequences were confirmed by in-house sequencing. None of these overlapping EST sequences in either the Incyte or publicly available databases were annotated by the producers of the sequence as being member of the TNF family of ligands. Also, no individual sequence among these sequences is sufficient to produce a soluble active form of the protein.

Example 2

Sequencing of EST-Containing Clones

DNA sequences for clones which comprise the most upstream ESTs of the contig are determined using dideoxy termination sequencing with either dye-labeled primers, dye terminators, or radiolabeled nucleotides, following known methods. See, for example, F. Sanger et al., *Proc. Natl. Acad. Sci. U.S.A.* 74:5463.

Because the vector pSPORT1 (Life Technologies, Gaithersburg, Md.) and pINCY, based on pSPORT-1 contains universal priming sites just adjacent to the 3' and 5' ligation junctions of the inserts, the inserts are sequenced in both directions using universal primers. The sequencing reactions are run on a polyacrylamide denaturing gel and the sequences are determined by an Applied Biosystems 377 Sequencer (available from Applied Biosystems, Foster City, Calif.) or other sequencing apparatus.

Based upon homology to other members of the TNF family of ligands, and the presence of an in-frame upstream stop codon, the sequence of clone ID #177393 (SEQUENCE ID NO 1) contains the entire TNF-gamma protein coding region(SEQUENC ID NO 2), and is therefore sufficient to form a biologically active molecule, one example of which is SEQUENCE ID NO 3.

Example 3

Nucleic Acid Preparation

A. RNA Extraction from Tissue. Total RNA is isolated from solid tissues or cells from patients with prostate cancer and non-tumor tissues using a lithium chloride/urea technique known in the art and described by N. Kato et al., *J. Virology* 61:2182–2191 (1987). Non-tumor tissues are used as negative controls. The mRNA can be further purified from total RNA using commercially available kits such as oligo dT cellulose spin columns (RediCol™ from Pharmacia, Uppsala, Sweden) for the isolation of poly-adenylated RNA. Total or mRNA then is dissolved in lysis buffer (5M guanidine thiocyanate, 0.1M EDTA, pH 7.0) for analysis in the ribonuclease protection assay.

B. RNA Extraction from Blood. RNA is prepared from blood samples from patients with or without diagnosed TNF-gamma associated disease by the standard QIAamp (Qiagen, Chattsworth, Calif.) RNA protocol. Briefly, 25 $\mu$l of blood are mixed with 280 $\mu$l of Qiagen AVL buffer and incubated at room temperature for 15 min. Then, 280 $\mu$l of 100% ethanol is added to the mixture and the entire mixture is transferred to a QIAamp spin column. Next, the column is spun at 6,000×g for 2 min, washed twice with 500 $\mu$l of Qiagen AW/ethanol buffer and spun at 6,000×g for 2 min. The column is spun an additional 3 min at >10,000×g. The RNA is eluted by adding 100 $\mu$l of RNase-free water preheated at 80° C. to the column and spinning at 6,000×g for 2 min.

C. RNA Extraction from polysomes. Tissue is minced in saline at 4° C. and mixed with 2.5 volumes of 0.8M sucrose in a $TK_{150}M$ (150 mM KCl, 5 mM $MgCl_2$, 50 mM Tris-HCl, pH 7.4) solution containing 6 mM 2-mercaptoethanol. The tissue is homogenized in a Teflon-glass Potter homogenizer with five strokes at 100–200 rpm followed by six strokes in a Dounce homogenizer, as described by B. Mechler, *Methods in Enzymology* 152:241–248 (1987). The homogenate then is centrifuged at 12,000×g for 15 min at 4° C. to sediment the nuclei. The polysomes are isolated by mixing 2 ml of the supernatant with 6 ml of 2.5M sucrose in $TK_{150}M$ and layering this mixture over 4 ml of 2.5M sucrose in $TK_{150}M$ in a 38 ml polyallomer tube. Two additional sucrose $TK_{150}M$ solutions are successively layered onto the extract fraction; a first layer of 13 ml 2.05M sucrose followed by a second layer of 6 ml of 1.3M sucrose. The polysomes are isolated by centrifuging the gradient at 90,000×g for 5 h at 4° C. The fraction then is taken from the 1.3M sucrose/2.05M sucrose interface with a siliconized pasteur pipette and diluted in an equal volume of TE (10 mM Tris-HCl, pH 7.4, 1 mM EDTA). An equal volume of 90° C. SDS buffer (1% SDS, 200 mM NaCl, 20 mM Tris-HCl, pH 7.4 is added and the solution is incubated in a boiling water bath for 2 min. Proteins next are digested with a proteinase-K digestion (50 mg/ml) for 15 min at 37° C. The mRNA is purified with 3 equal volumes of phenol-chloroform extractions followed by precipitation with 0.1 volume of 2M sodium acetate (pH 5.2) and 2 volumes of 100% ethanol at −20° C. overnight. The precipitated RNA is recovered by centrifugation at 12,000×g for 10 min at 4° C. The RNA is dried and resuspended in TE, pH 7.4 or distilled water. The resuspended RNA then can be used in a slot blot or dot blot hybridization assay to check for the presence of mRNA containing EST sequences (see example 6).

The quality of nucleic acid and proteins is dependent on the method of preparation used. Each sample may require a different preparation technique to maximize isolation efficiency of the target molecule.

Example 4

Ribonuclease Protection Assay

A. Labeling of Complementary RNA (cRNA) Hybridization Probes Labeled sense and antisense riboprobes are transcribed from the EST sequence which contains a 5' RNA polymerase promoter such as SP6 or T7. The sequence may be from a vector containing the appropriate EST insert or from a PCR-generated product of the insert using PCR primers which incorporate a 5' RNA polymerase promoter sequence. The transcripts are prepared in a 20 µl reaction volume containing 1 µg of DNA template, 2 µl of 100 mM dithiothreitol, 0.8 µl of RNasin (10-40U), 500 µM each of ATP, CTP, GTP, 5 µl (alpha$^{32}$P) UTP or 100–500 µM biotinylated UTP, and 1 µl of RNA polymerase in transcription buffer (40 mM Tris-HCl, pH 7.5, 6 mM MgCl$_2$, 2 mM spermidine HCl, 5 mM NaCl). Following incubation at 37° C. for one hour, the transcripts are treated with DNase I (15 U) for an additional 30 min to digest the template. The probes then are isolated by spin columns, salt precipitation or electrophoresis techniques which are well-known in the art. Finally, the probes are dissolved in lysis buffer (5M Guanidine Thiocyanate, 0.1M EDTA, pH 7.0).

B. Hybridization of Labeled Probe to Target. Approximately 20 µg of extracted total cellular RNA, as obtained in Example 3 supra, in 10 µl of lysis buffer are mixed with either (i) 1×10$^5$ cpm of radioactively labeled probe or (ii) 250 pg of non-isotopically labeled probe, each in 2 µl of lysis buffer. The mixture then is incubated at 6020 C. for 5 min and hybridized overnight at room temperature. See, T. Kaabache et al., *Anal. Biochem.* 232:225–230 (1995).

C. RNase Digestion. Hybridizations are terminated by incubation with 380 µl of a solution containing 40 µg/ml RNase A and 625 units/ml RNase T1 in 1 mM EDTA, 300 mM NaCl, 30 mM Tris-HCl pH 7.4 for 45–60 min at room temperature. RNase digestion then is terminated by the addition of 60 µl of proteinase-K (1.7 mg/ml) containing 3.3% SDS, followed by incubation for 30 min at 37° C. The digested mixture then is extracted with phenol:chloroform:isoamyl alcohol to remove protein. The mRNA:cRNA hybrids are precipitated from the aqueous phase by the addition 4 µg yeast tRNA and 800 µl of ethanol, and incubation at −80° C. for 30 min. The precipitates are collected by centrifugation.

D. Fragment Analysis. The precipitates are dissolved in 5 µl of denaturing gel loading dye (80% formamide, 10 mM EDTA, pH 8.0, 1 mg/ml xylene cyanol, 1 mg/ml bromophenol blue) and electrophoresed in 6 % polyacrylamide TBE, 8M urea denaturing gels. The gels are dried under vacuum and autoradiographed. Quantitation can be performed by comparing the counts obtained from the test samples to a calibration curve that was generating by utilizing calibrators that are the sense strand. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents. High level of expression of mRNA corresponding to a sequence selected from the group consisting of SEQUENCE ID NO 1, or fragments or complements thereof, then is an indication of the presence of TNF-gamma gene.

Example 5

Northern Blotting

The northern blot technique is used to identify a specific size RNA fragment from a complex population of RNA using gel electrophoresis and nucleic acid hybridization. Northern blotting is well-known technique in the art. Briefly, up to 20 µg of extracted RNA (see Example 3) are incubated in 20 µl of a solution containing 40 mM morphilinopropanesulfonic acid (MOPS), pH 7.0, 10 mM sodium acetate, 1 mM EDTA, 2.2M formaldehyde, 50% v/v formamide for 15 min at 55° C. The denatured RNA is mixed with 2 µl of loading buffer (50% glycerol, 1 mM EDTA, 0.4% bromophenol blue, 0.4% xylene cyanol) and loaded into a denaturing 1.5% agarose gel containing 40 mM morphilinopropanesulfonic acid (MOPS), pH 7.0, 10 mM sodium acetate, 1 mM EDTA and 2.2M formaldehyde. The gel is electrophoresed for an appropriate time, transferred to a wash tray and washed with five changes of RNase free water for 5 min followed by a 45 min soak at room temperature in 50 mM NaOH and 10 mM NaCl. The gel is neutralized by soaking for 45 min in 0.1M Tris-HCl, pH 7.5. After a 1 h soak in 20× SSC buffer (3M NaCl, 300 mM tri-sodium citrate), the gel is transferred onto a nitrocellulose or nylon based matrix. After transfer is complete, the filter is washed in 3× SSC, air dried for 2 h and baked at 80° C. for 4 h under vacuum. The mRNAs are detected as in example 4, supra. Again, high level of expression of mRNA corresponding to SEQUENCE ID NO 1 and fragments or complements thereof, is an indication of the presence of the TNF-gamma gene.

Example 6

Dot Blot/Slot Blot

Dot and slot blot assays are quick methods to evaluate the presence of a specific nucleic acid sequence in a complex mix of nucleic acid.

To perform, up to 20 µg of RNA is mixed in 50 µl of 50% formamide, 7% formaldehyde, 1× SSC, incubated 15 min at 68° C. and cooled on ice. Then, 100 µl of 20× SSC is added to the RNA mixture and loaded under vacuum onto a manifold apparatus that has a prepared nitrocellulose or nylon membrane. The membrane is soaked in water, 20× SSC for 1 hour, placed on two sheets of 20× SSC prewet Whatman #3 filter paper, and loaded into a slot blot or dot blot vacuum manifold apparatus. The slot blot is analyzed with probes prepared and labeled as in the example 4 supra. Detection of mRNA corresponding to SEQUENCE ID NO 1 and fragments or complements thereof, is an indication of the presence of the TNF-gamma gene, suggesting the diagnosis of inflammatory disease.

Other methods and buffers not specifically detailed for examples 5 and 6 are described in J. Sambrook et al, supra.

Example 7

In Situ Hybridization

This method is useful to directly detect specific target nucleic acid sequences in cells using detectable nucleic acid hybridization probes.

Tissues are prepared with cross-linking fixatives agents such as paraformaldehyde or glutaraldehyde for maximum cellular RNA retention. See, L. Angerer et al., *Methods in Cell Biol.* 35:37–71 (1991). Briefly, the tissue is placed in greater than 5 volumes of 1% glutaraldehyde in 50 mM sodium phosphate, pH 7.5 at 4° C. for 30 min. The solution is changed with fresh solution for a further 30 min fixing. The fixing solution should have an osmolality of approximately 0.375% NaCl. The tissue is washed once in isotonic NaCl to remove the phosphate.

The fixed tissues then are embedded in paraffin, as follows. The tissue is dehydrated though a series of ethanol concentrations for 15 min each: 50% twice, 70% twice, 85%, 90% and 100% twice. The tissue next is soaked in two changes of xylene for 20 min each at room temperature; then it is soaked in two changes of 1 xylene:1 paraffin for 20 min each at 60° C.; and then it is soaked in three final changes in paraffin for 15 min each.

The tissue next is cut in 5 µm sections using a standard microtome and placed on a slide previously treated with the tissue adhesive 3-aminopropyltriethoxysilane.

Paraffin is removed from the tissue by two 10 min xylene soaks and rehydrated in a series of ethanol concentrations; 99% twice, 95%, 85%, 70%, 50%, 30% and distilled water twice. The sections are pre-treated with 0.2M HCl for 10 min and permeabilized with 2 µg/ml Proteinase-K at 37° C. for 15 min.

Labeled riboprobes transcribed from the EST pSPORT1 plasmid (see example 4) are hybridized to the prepared tissue sections and hybridized overnight at 56° C. in 3× standard saline extract and 50% formamide. Excess probe is removed by washing in 2× standard saline citrate and 50% formamide followed by digestion with 100 µg/ml RNase A at 37° C. for 30 min. Fluorescence probe is visualized by illumination with UV light under a microscope. Fluorescence in the cytoplasm is indicative of mRNA production. Fluorescence in the nucleus detects the presence of genomic material. Alternatively, the sections can be visualized by autoradiography.

Example 8

Reverse Transcription PCR

A. One Step RT-PCR Assay. Target-specific primers are designed to detect the above target sequence by reverse transcription PCR by methods known in the art. One step RT-PCR is a sequential procedure that performs both RT and PCR in a single reaction mixture. The procedure is performed in a 200 µl reaction mixture containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 µM each of dNTP, 0.25 µM each primer, 5U rTth polymerase, 3.25 mM Mn(OAc)$_2$, and 5 µl blood equivalents of target (see example 3). Since RNA and the rTth polymerase enzyme are unstable in the presence of Mn(OAc)$_2$, the Mn(OAc)$_2$ should be added just before target addition. Optimal conditions for cDNA synthesis and thermal cycling readily can be determined by those skilled in the art. The reaction is incubated in a Perkin-Elmer Thermal Cycler 480. Optimal conditions for cDNA synthesis and thermal cycling can readily be determined by those skilled in the art. Conditions which may be found useful include cDNA synthesis at 60°–70° for 15–45 min, and 30–45 amplification cycles at 94° C., 1 min; 55° C.–70° C., 1 min; 72° C., 2 min. One step RT-PCR also may be performed by using a dual enzyme procedure with Taq polymerase and a reverse transcriptase enzyme, such as MMLV or AMV RT enzymes.

B. Traditional RT-PCR. Alternatively, a traditional two step RT-PCR reaction may be performed, as described by K.-Q. Hu et al., *Virology* 181:721–726 (1991), as follows: The extracted mRNA is transcribed in a 25 µl reaction mixture containing 10 mM Tris-HCl, pH 8.3, 5 mM MgCl$_2$, 500 µM dNTP, 20 U RNasin, 1 µM antisense primer, and 25 U AMV (avian myeloblastosis virus) or MMLV (Moloney murine leukemia virus) reverse transcriptase. Reverse transcription is performed at 37–45° C. for 30–60 min, followed by further incubation at 95° C. for 5 min to inactivate the RT. PCR is performed using 10 µl of the cDNA reaction in a final PCR reaction volume of 50 µl containing 10 mM Tris-HCl, pH 8.3, 50 mM KCl, 2 mM MgCl$_2$, 200 µM dNTP, 0.5 µM of each primer and 2.5 U of Taq polymerase. Optimal conditions for cDNA synthesis and thermal cycling can be readily determined by those skilled in the art. The reaction is incubated in a Perkin-Elmer Thermal Cycler 480. Conditions which may be found useful include 30–45 cycles of amplification (94° C., 1 min; 55°–70° C., 1 min; 72° C., 2 min), final extension (72° C., 10 min) and soak at 4° C.

C. PCR Fragment Analysis. The correct products can then be verified by size determination using gel electrophoresis with fluorescent intercalators or by southern blotting techniques using a labeled probes against the internal sequences of the PCR product. The probes may also be polynucleotides analogs, such as morpholinos or peptide nucleic acids (PNA). Detection of SEQUENCE ID NO 1 and/or fragments or complements thereof is then indicative of the presence of the TNF-gamma gene, suggesting the diagnosis of inflammatory disease.

D. Automated Ouantitative PCR. Quantities of specific PCR products in a given sample can be automatically verified by using a fluorescently labeled probe against the internal sequences of the PCR product coupled to a quenching moiety. Uncoupling of the fluorescent tag to the quenching moiety from the internal probe hybridized to the PCR product by the PCR polymerase during thermocycling can be detected by machines such as the Perkin-Elmer 7700 quantitative PCR machine, and is proportional to the amount of PCR product present in the sample. Detection of SEQUENCE ID NO 1 and/or fragments or complements thereof is then indicative of the presence of the TNF-gamma gene, suggesting the diagnosis of inflammatory disease.

Example 9

OH-PCR

A. Probe selection and Labeling. Target-specific primers and probes are designed to detect the above target sequence by oligonucleotide hybridization PCR. Publications WO 92/10505, published Jun. 25, 1992 and WO 92/11388 published Jul. 9, 1992 (equivalent to U.S. Pat. No. 5,290,925, issued Mar. 1, 1994) teach methods for labeling oligonucleotides at their 5' and 3' ends, respectively. According to one known method for labeling an oligonucleotide, a label-phosphoramidite reagent is prepared and used to add the label to the oligonucleotide during its synthesis. For example, see N. T. Thuong et al., *Tet. Letters* 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' end to prevent participation in PCR and the formation of undesired extension products. For one step OH-PCR the probe should have a $T_M$ at least 15° C. below the $T_M$ of the primers. The primers and probes are labeled with either capturable or detectable moieties using standard phosphoramidite chemistry which is well-known to one skilled in the art.

B. One Step Oligo Hybridization PCR. OH-PCR is performed on a 200 µl reaction containing 50 mM (N,N,-bis [2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 µM each of dNTP, 0.25 µM each primer, 3.75 nM probe, 5U rTth polymerase, 3.25 mM Mn(OAc)$_2$, and 5 µl blood equivalents of target (see example 3). Since RNA and the rTth polymerase enzyme are unstable in the presence of Mn(OAc)$_2$, the Mn(OAc)$_2$ should be added just before target addition. The reaction is incubated in a Perkin-Elmer Thermal Cycler 480. Optimal conditions for cDNA synthesis and thermal cycling can be readily determined by those skilled in the art. Conditions which may be found useful include cDNA synthesis (60° C., 30 min), 30–45 amplification cycles (94° C., 40 sec; 55–70° C., 60 sec), oligo-hybridization (97° C., 5 min; 15° C., 5 min; 15° C. soak). The correct reaction product contains at least one of the strands of the PCR product and an internally hybridized probe.

C. OH-PCR product analysis. Amplified reaction products are detected on an LCx® analyzer system (available from Abbott Laboratories, Abbott Park, Ill.). Briefly, the correct reaction product is captured by an antibody labeled microparticle at a capturable site on either the PCR product strand or the hybridization probe, and the complex is detected by binding of a detectable antibody conjugate to either a detectable site on the probe or the PCR strand. Only a complex containing a PCR strand hybridized with the internal probe is detectable. The detection of this complex is then indicative of the presence of the TNF-gamma gene, suggesting the diagnosis of inflammatory disease, such as rheumatoid arthritis.

Many other detection formats exist which can be used to detect the presence of the TNF-gamma encoding nucleic acid sequence. The sequence may also be detected by other methods including but not limited to, ligase chain reaction (LCR, Abbott Laboratories, Abbott Park, Ill.); Q-beta replicase (Gene-Trak™, Naperville, Ill.), branched chain reaction (Chiron, Emeryville, Calif.), and strand displacement assays (Becton Dickinson, Research Triangle Park, N.C.).

Example 10

Synthetic Peptide Production

Synthetic peptides are prepared based upon the predicted amino acid sequence of the TNF-gamma polypeptide (see example 1). All peptides are synthesized on an ABI Peptide Synthesizer (available from Applied Biosciences, LOCATION), Model 431A, using FMOC chemistry, standard cycles and DCC-HOBt activation. Cleavage and deprotection conditions are as follows: the resin is added to 20 ml trifluoroacetic acid (TFA), 0.3 ml water, 0.2 ml ethanedithiol, 0.2 ml thioanisole and 100 mg phenol, and stirred at room temperature for 1.5 hours. The resin then is filtered by suction and the peptide is obtained by precipitation of the TFA solution with ether followed by filtration. Each peptide is purified via reverse-phase preparative HPLC using a water/acetonitrile/0.1% TFA gradient and lyophilized. The product is confirmed by mass spectrometry (see example 12).

Disulfide bond formation is accomplished using autooxidation conditions, as follows: the peptide is dissolved in a minimum amount of DMSO (approximately 10 ml) before adding buffer (0.1M Tris-HCl, pH 6.2) to a concentration of 0.3–0.8 mg/ml. The reaction is monitored by HPLC until complete formation of the disulfide bond, followed by reverse-phase preparative HPLC using a water/acetonitrile/0.1% TFA gradient and lyophilization. The product then is confirmed by mass spectrometry (see example 12).

The purified peptides can be conjugated to Keyhole Limpet Hemocyanin or other immunoreactive molecule with glutaraldehyde, mixed with adjuvant, and injected into animals.

Example 11

Expression of Protein in a Cell Line

A. Construction of EST Expression Plasmid. Plasmid 577, described in U.S. Pat. No. 6,020,122, issued Feb. 1, 2000, and incorporated herein by reference, has been constructed for the expression of secreted antigens in a permanent cell line. This plasmid contains the following DNA segments: (a) a 2.3 Kb fragment of pBR322 containing bacterial beta-lactamase and origin of DNA replication; (b) a 1.8 Kb cassette directing expression of a neomycin resistance gene under control of HSV-1 thymidine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a rabbit immunoglobulin heavy chain signal sequence fused to a modified hepatitis C virus (HCV) E2 protein under the control of the Simian Virus 40 T-Ag promoter and transcription enhancer, the hepatitis B virus surface antigen (HBsAg) enhancer I followed by a fragment of Herpes Simplex Virus-1 (HSV-1) genome providing poly-A addition signals; and (e) a residual 0.7 Kb fragment of Simian Virus 40 genome late region of no function in this plasmid. All of the segments of the vector were assembled by standard methods known to those skilled in the art of molecular biology.

Plasmids for the expression of secretable TNF gamma proteins are constructed by replacing the hepatitis C virus E2 protein coding sequence in plasmid 577 with those from the EST sequence selected from the group consisting of SEQUENCE ID NO 1 or fragments thereof, as follows. Digestion of plasmid 577 with XbaI releases the hepatitis C virus E2 gene fragment. The resulting plasmid backbone allows insertion of the TNF-gamma insert downstream of the rabbit immunoglobulin heavy chain signal sequence which directs the expressed proteins into the secretory pathway of the cell. The TNF-gamma fragment is generated by PCR using standard procedures. Encoded in the sense PCR primer sequence is an Xba 1 site, immediately followed by a 12 nucleotide sequence that encodes the amino acid sequence Ser-Asn-Glu-Leu ("SNEL"; SEQUENCE ID NO 13) to promote signal protease processing, efficient secretion and final product stability in culture fluids. Immediately following this 12 nucleotide sequence the primer contains nucleotides complementary to template sequences encoding amino acids of the TNF-gamma sequence. The antisense primer incorporates a sequence encoding the eight amino acids Asp-Tyr-Lys-Asp-Asp-Asp-Asp-Lys (SEQUENCE ID NO 5) just before the stop codons. Within this sequence is the recognition site for a monoclonal antibody (MAb) designated anti-FLAG M2 (Eastman Kodak, Co., New Haven, Conn.). It is incorporated to aid in analysis and purification of the EST protein product. PCR is performed using Gene-Amp® reagents obtained from Perkin-Elmer-Cetus, essentially as directed by the supplier's instructions. PCR primers are used at a final concentration of 0.5 $\mu$M. PCR is performed on the pSPORT1 plasmid template in a 100 $\mu$l reaction for 35 cycles (94° C., 30 seconds; 55° C., 30 seconds; 72° C., 90 seconds) followed by an extension cycle of 72° C. for 10 min.

Another example of a plasmid for the expression of secretable TNF-gamma proteins is placing fusing in-frame sequence encoding the human serum albumin leader sequence (SEQUENCE ID NO 4) to the synthetic octapeptide encoding the eight amino acids eight amino acids Asp-Tyr-Lys-Asp-Asp-Asp-Asp-Lys (recognized by the monoclonal antibody designated anti-FLAG M2; SEQUENCE ID NO 5) followed by an appropriate carboxyl-terminal portion of TNF-gamma which interacts with the cognate receptor, and can therefore induce biological activity (SEQUENCE ID NO 3). One such form of soluble TNF-gamma is presented in SEQUENCE ID NO 3. This engineered synthetic open reading frame (SEQUENCE ID NO 4+SEQUENCE ID NO 5+SEQUENCE ID NO 3) can be placed in an appropriate DNA backbone as is appropriate for the intended target cell, such as pcDNA3 (Invitrogen Corp, San Diego, Calif.).

B. Transfection of Dihydrofolate Reductase Deficient Chinese Hamster Ovary Cells. The plasmids described supra is transfected into CHO/dhfr-cells (DXB-111) (Uriacio et al., *PNAS* 77, 4451–4466; 1980); these cells are available from the A.T.C.C., 12301 Parklawn Drive, Rockville, Md. 20852, under Accession No. CRL 9096), using the cationic liposome-mediated procedure (P. L. Felgner et al., *PNAS* 84:7413–7417 [1987]), as follows. CHO/dhfr-cells are cultured in Ham's F-12 media supplemented with 10% fetal calf serum, L-glutamine (1 mM) and freshly seeded into a 25 $cm^2$ flask at a density of $5–8\times10^5$ cells per flask. The cells are grown to between 60 and 80% confluency for transfection. Twenty micrograms of plasmid DNA are added to 1.5 ml of Opti-MEM I medium and 100 $\mu$l of Lipofectin Reagent (Gibco-BRL; Grand Island, N.Y.) are added to a second 1.5 ml portion of Opti-MEM I media. The two solutions are mixed and incubated at room temperature for 20 min. The culture medium is removed from cells and the cells are rinsed 3 times with 5 ml of Opti-MEM I medium. The Opti-MEM I-Lipofection-plasmid DNA solution is then overlaid onto the cells. The cells are incubated for 3 h at 37° C., after which time the Opti-MEM I-Lipofectin-DNA solution is replaced with culture medium for an additional 24 h prior to selection.

C. Selection and Amplification. One day after transfection, cells are passaged 1:3 and incubated with dhfr/G418 selection medium (hereafter, "F-12 minus medium G"). Selection medium is Ham's F-12 with L-glutamine and without hypoxanthine, thymidine, and glycine (JRH Biosciences, Lenexa, Kans.), and 300 $\mu$g per ml G418 (Gibco-BRL; Grand Island, N.Y.). Media volume to surface area ratios of 5 ml per 25 $cm^2$ are maintained. After approximately two weeks, DHFR/G418 cells are expanded to allow passage and continuous maintenance in F-12 minus medium G.

Amplification of each of the transfected EST genes is achieved by stepwise selection of $DHFR^+$, $G418^+$ cells with methotrexate (reviewed by R. Schimke, *Cell* 37:705–713 [1984]). Cells are incubated with F-12 minus medium G containing 150 nM methotrexate (MTX) (Sigma, St. Louis, Mo.) for approximately two weeks until resistant colonies appear. Further gene amplification is achieved by selection of 150 nM adapted cells with 5 $\mu$M MTX.

D. Protein/Antigen Production. F-12 minus medium G supplemented with 5 $\mu$M MTX is overlaid onto just confluent monolayers for 12 to 24 h at 37° C. in 5% $CO_2$. The growth medium is removed and the cells are rinsed 3 times with Dulbecco's phosphate buffered saline (PBS) (with calcium and magnesium) (Gibco-BRL; Grand Island, N.Y.), to remove the remaining media/serum which might be present. Cells then are incubated with VAS custom medium (VAS custom formulation with L-glutamine with HEPES without phenol red, available from JRH Bioscience; Lenexa, Kans., product number 52-08678P), for 1 h at 37° C. in 5% $CO_2$. Cells then are overlaid with VAS for production at 5 ml per T 25 $cm^2$ flask. The medium is removed after 7 days of incubation and then frozen to await purification with harvests 2, 3 and 4. The monolayers are overlaid with VAS for 3 more 7-day harvests.

E. Analysis of TNF-gamma Protein/Antigen Expression. Aliquots of VAS supernatants from the cells expressing the engineered protein construct are analyzed either by SDS-polyacrylamide gel electrophoresis (SDS-PAGE) using standard methods and reagents known in the art (Laemmli discontinuous gels) or by mass spectrometry.

F. Purification. Purification of the EST protein containing the FLAG sequence is performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, protein in pooled VAS medium harvests from roller bottles is exchanged into 50 mM Tris-HCl pH 7.5, 150 mM NaCl buffer using a Sephadex G-25 (Pharmacia Biotech Inc., Uppsala, Sweden) column. Protein in this buffer is applied to the anti-FLAG M2 antibody affinity column, non-binding protein is eluted by washing the column with 50 mM Tris-HCl pH 7.5, 150 mM NaCl buffer and bound protein is eluted using an excess of FLAG peptide in 50 mM Tris-HCl, pH 7.5, 150 mM NaCl. The excess FLAG peptide can be removed from the EST purified protein by gel electrophoresis.

Then, the largest cloned insert containing the EST region is sub-cloned into either (i) a eukaryotic expression vector which may contain a cytomegalovirus (CMV) promoter and/or protein fusable sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in European Patent No. 196056B1, and those of CKS are described in European Patent No. 331961B1. The purified protein can be used in a variety of techniques, including but not limited to animal immunization studies, solid phase immunoassays, etc.

Example 12

Chemical Analysis of TNF-Gamma Proteins

A. Analysis of Tryptic Peptide Fragments Using MS. Serum from a patient with inflammatory disease is run on a polyacrylamide gel using standard procedures and stained with Coomassie Blue. Sections of the gel suspected of containing the unknown polypeptide are excised and subjected to an in-gel reduction, acetamidation, and tryptic digestion. P. Jeno et al, *Anal. Bio.* 224:451–455 (1995), and J. Rosenfeld et al, *Anal. Bio.* 203:173–179 (1992). The gel sections are washed with 100 mM $NH_4HCO_3$ and acetonitrile. The shrunken gel pieces are swollen in digestion buffer (50 mM $NH_4HCO_3$, 5 mM $CaCl_2$, and 12.5 µg/ml trypsin) at 4° C. for 45 min. The supernatant is aspirated and replaced with 5 to 10 µl of digestion buffer without trypsin and allowed to incubate overnight at 37° C. Peptides are extracted with 3 changes of 5% formic acid and acetonitrile, and evaporated to dryness. The peptides are adsorbed to approximately 0.1 µl of POROS R2 sorbent (Perseptive Biosystems, Framingham, Mass.) trapped in the tip of a drawn gas chromatography capillary tube by dissolving them in 10 µl of 5% formic acid and passing it through the capillary. The adsorbed peptides are washed with water and eluted with 5% formic acid in 60% methanol. The eluant is passed directly into the spraying capillary of an API III mass spectrometer (Perkin-Elmer Sciex, Thornhill, Ontario, Canada) for analysis by nano-electrospray mass spectrometry. M. Wilm et al., *Int. J. Mass Spectrom. Ion Process* 136:167–180 (1994), and M. Wilm et al., *Anal. Chem.* 66:1–8 (1994). The masses of the tryptic peptides are determined from the mass spectrum obtained off the first quadrupole. Masses corresponding to predicted peptides can be further analyzed in MS/MS mode to give the amino acid sequence of the peptide.

B. Peptide Fragment Analysis Using LC/MS. The presence of polypeptides predicted from mRNA sequences found in hyperplastic disease tissues also can be confirmed using liquid chromatography/tandem mass spectrometry (LC/MS/MS). D. Hess et al., *METHODS, A Companion to Methods in Enzymology* 6:227–238 (1994). The serum specimen or tumor extract from the patient is denatured with SDS and reduced with dithiothreitol (1.5 mg/ml) for 30 min at 90° C. followed by alkylation with iodoacetamide (4 mg/ml) for 15 min at 25° C. Following acrylamide electrophoresis, the polypeptides are electroblotted to a cationic membrane and stained with Coomassie Blue. Following staining, the membranes are washed and sections thought to contain the unknown polypeptides are cut out and dissected into small pieces. The membranes are placed in 500 µl microcentrifuge tubes and immersed in 10 to 20 µl of proteolytic digestion buffer (100 mM Tris-HCl, pH 8.2, containing 0.1M NaCl, 10% acetonitrile, 2 mM $CaCl_2$, and 5 µg/ml trypsin) (Sigma, St. Louis, Mo.). After 15 h at 37° C., 3 µl of saturated urea and 1 µl of 100 µg/ml trypsin are added, and incubated for an additional 5 h at 37° C. The digestion mixture is acidified with 3 µl of 10% trifluoroacetic acid and centrifuged to separate supernatant from membrane. The supernatant is injected directly onto a microbore, reverse phase HPLC column and eluted with a linear gradient of acetonitrile in 0.05% trifluoroacetic acid. The eluate is fed directly into an electrospray mass spectrometer, after passing though a stream splitter if necessary to adjust the volume of material. The data is analyzed following the procedures set forth in example 12, section A.

Example 13

Gene Immunization Protocol

A. In Vivo Antigen Expression. Gene immunization circumvents protein purification steps by directly expressing an antigen in vivo after inoculation of the appropriate expression vector. Also, production of antigen by this method may allow correct protein folding and glycosylation since the protein is produced in mammalian tissue. The method utilizes insertion of the gene sequence into a plasmid which contains a CMV promoter, expansion and purification of the plasmid, and injection of the plasmid DNA into the muscle tissue of an animal. See, for example, H. Davis et al., *Human Molecular Genetics* 2:1847–1851 (1993). After one or two booster immunizations, the animal can then be bled, ascites fluid collected or spleen harvested for production of hybridomas.

B. Plasmid Preparation and Purification. EST DNA sequences are generated from the pSPORT1 EST vector using appropriate PCR primers containing suitable 5' restriction sites. The PCR product is cut with appropriate restriction enzymes and inserted into a vector which contains the CMV promoter (for example, pRc/CMV or pcDNA3 vectors from Invitrogen, San Diego, Calif.). This plasmid then is expanded in the appropriate bacterial strain and purified from the cell lysate using a CsCl gradient or a Qiagen plasmid DNA purification column. All these techniques are familiar to one of ordinary skill in the art of molecular biology.

C. Immunization Protocol. Anesthetized animals are immunized intramuscularly with 0.1–100 µg of the purified plasmid diluted in PBS or other DNA uptake enhancers (Cardiotoxin, 25% sucrose). See, for example, H. Davis et al. *Human Gene Therapy* 4:733–740 (1993); and P. W. Wolff et al, *Biotechniques* 11:474–485 (1991). One to two booster injections are given at monthly intervals.

D. Testing and Use of Antiserum. Animals are bled and the sera tested for antibody using peptides synthesized from the known gene sequence (see example 16) such as western blotting or EIA techniques. Antisera produced by this method can then be used to detect the presence of the antigen in a patient's sera or tumor tissue extract by ELISA or Western blotting techniques.

Example 14

Production of Antibodies Against TNF-Gamma

A. Production of Polyclonal Antisera. Antiserum against PS108 is prepared by injecting appropriate animals with peptides whose sequences are derived from that of the TNF-gamma sequence (SEQUENCE ID NO 2). The synthesis of the peptides is described in Example 10. Peptides used as immunogen either can be conjugated to a carrier such as keyhole limpet hemocyanine (KLH), prepared as described hereinbelow, or unconjugated (i.e., not conjugated to a carrier such as KLH).

1. Peptide Conjugation. Peptide is conjugated to maleimide activated keyhole limpet hemocyanine (KLH, commerically available as Imject®, available from Pierce Chemical Company, Rockford, Ill.). Imject® contains about 250 moles of reactive maleimide groups per mole of hemocyanine. The activated KLH is dissolved in phosphate buffered saline (PBS, pH 8.4) at a concentration of about 7.7 mg/ml. The peptide is conjugated through cysteines occurring in the peptide sequence or to a cysteine previously added to the synthesized peptide in order to provide a point of attachment. The peptide is dissolved in dimethyl sulfoxide (DMSO, Sigma Chemical Company, St. Louis, Mo.) and reacted with the activated KLH at a mole ratio of about 1.5 moles of peptide per mole of reactive maleimide attached to the KLH. A procedure for the conjugation of peptide is provided hereinbelow. It is known to the ordinary artisan that the amounts, times and conditions of such a procedure can be varied to optimize peptide conjugation.

The conjugation reaction described hereinbelow is based on obtaining 3 mg of KLH peptide conjugate ("conjugated peptide"), which contains about 0.77 μmoles of reactive maleimide groups. This quantity of peptide conjugate usually is adequate for one primary injection and four booster injections for production of polyclonal antisera in a rabbit. Briefly, peptide is dissolved in DMSO at a concentration of 1.16 μmoles/100 μl of DMSO. 100 μl of the DMSO solution is added to 380 μl of the activated KLH solution prepared as described hereinabove, and 20 μl of PBS (pH 8.4) is added to bring the volume to 500 μl. The reaction is incubated overnight at room temperature with stirring. The extent of reaction is determined by measuring the amount of unreacted thiol in the reaction mixture. The difference between the starting concentration of thiol and the final concentration is assumed to be the concentration of peptide which has coupled to the activated KLH. The amount of remaining thiol is measured using Ellman's reagent (5,5'-dithiobis(2-nitrobenzoic acid), Pierce Chemical Company, Rockford, Ill.). Cysteine standards are made at a concentration of 0, 0.1, 0.5, 2, 5 and 20 mM by dissolving 35 mg of cysteine HCl (Pierce Chemical Company, Rockford, Ill.) in 10 ml of PBS (pH 7.2) and diluting the stock solution to the desired concentration(s). The photometric determination of the concentration of thiol is accomplished by placing 200 μl of PBS (pH 8.4) in each well of an Immulon 2® microwellplate (Dynex Technologies, Chantilly, Va.). Next, 10 μl of standard or reaction mixture is added to each well. Finally, 20 μl of Ellman's reagent at a concentration of 1 1 mg/ml in PBS (pH 8.4) is added to each well. The wells are incubated for 10 minutes at room temperature, and the absorbance of all wells is read at 415 nm with a microplate reader (such as the BioRad Model 3550, BioRad, Richmond, Calif.). The absorbance of the standards is used to construct a standard curve and the thiol concentration of the reaction mixture is determined from the standard curve. A decrease in the concentration of free thiol is indicative of a successful conjugation reaction. Unreacted peptide is removed by dialysis against PBS (pH 7.2) at room temperature for 6 hours. The conjugate is stored at 2–8° C. if it is to be used immediately; otherwise, it is stored at −20° C. or colder.

2. Animal Immunization. Female white New Zealand rabbits weighing 2 kg or more are used for raising polyclonal antiserum. Generally, one animal is immunized per unconjugated or conjugated peptide (prepared as described hereinabove). One week prior to the first immunization, 5 to 10 ml of blood is obtained from the animal to serve as a non-immune prebleed sample.

Unconjugated or conjugated peptide is used to prepare the primary immunogen by emulsifying 0.5 ml of the peptide at a concentration of 2 mg/ml in PBS pH 7.2 and which also contained 0.5 ml of complete Freund's adjuvant (CFA) (Difco, Detroit, Mich.). The immunogen is injected into several sites of the animal, and injections can include subcutaneous, intraperitoneal and intramuscular. Four weeks following the primary immunization, a booster immunization is administered. The immunogen used for the booster immunization dose is prepared by emulsifying 0.5 ml of the same unconjugated or conjugated peptide used for the primary immunogen, except that the peptide now is diluted to 1 mg/ml with 0.5 ml of incomplete Freund's adjuvant (IFA) (Difco, Detroit, Mich.). Again, the booster dose is administered into several sites and can utilize subcutaneous, intraperitoneal and intramuscular types of injections. The animal is bled (5 ml) two weeks after the booster immunization and the serum is tested for immunoreactivity to the peptide, as described below. The booster and bleed schedule is repeated at 4 week intervals until an adequate titer is obtained. The titer or concentration of antiserum is determined by microtiter EIA as described in Example 17, below. An antibody titer of 1:500 or greater is considered an adequate titer for further use and study.

B. Production of Monoclonal Antibody

1. Immunization Protocol. Mice are immunized using immunogens prepared as described hereinabove, except that the amount of the unconjugated or conjugated peptide for monoclonal antibody production in mice is one-tenth the amount used to produce polyclonal antisera in rabbits. Thus, the primary immunogen consists of 100 μg of unconjugated or conjugated peptide in 0.1 ml of CFA emulsion; while the immunogen used for booster immunizations consists of 50 μg of unconjugated or conjugated peptide in 0.1 ml of IFA. Hybridomas for the generation of monoclonal antibodies are prepared and screened using standard techniques. The methods used for monoclonal antibody development follow procedures known in the art and detailed in Kohler and Milstein, *Nature* 256:494 (1975) and reviewed in J. G. R. Hurrel, ed., *Monoclonal Hybridoma Antibodies: Techniques and Applications*, CRC Press, Inc., Boco Raton, Fla. (1982). Another method of monoclonal antibody development which is based on the Kohler and Milstein method is that of L. T. Mimms et al., *Virology* 176:604–619 (1990), which is incorporated herein by reference.

The immunization regimen (per mouse) consists of a primary immunization with additional booster immunizations. The primary immunogen used for the primary immunization consists of 100 μg of unconjugated or conjugated peptide in 50 μl of PBS (pH 7.2) previously emulsified in 50 μl of CFA. Booster immunizations performed at approximately two weeks and four weeks post primary immunization consist of 50 μg of unconjugated or conjugated peptide in 50 μl of PBS (pH 7.2) emulsified with 50 μlIFA. A total of 100 μl of this immunogen is inoculated intraperitoneally and subcutaneously into each mouse. Individual mice are screened for immune response by microtiter plate enzyme immunoassay (EIA) as described in Example 17 approximately four weeks after the third immunization. Mice are inoculated either intravenously, intrasplenically or intraperitoneally with 50 μg of unconjugated or conjugated peptide in PBS (pH 7.2) approximately fifteen weeks after the third immunization.

Three days after this intravenous boost, splenocytes are fused with, for example, Sp2/0-Ag14 myeloma cells (Milstein Laboratories, England) using the polyethylene glycol (PEG) method. The fusions are cultured in Iscove's Modified Dulbecco's Medium (IMDM) containing 10% fetal calf serum (FCS), plus 1% hypoxanthine, aminopterin and thymidine (HAT). Bulk cultures are screened by microtiter plate EIA following the protocol in Example 17. Clones reactive with the peptide used an immunogen and non-reactive with other peptides (i.e., peptides of PS108 not used as the immunogen) are selected for final expansion. Clones thus selected are expanded, aliquoted and frozen in IMDM containing 10% FCS and 10% dimethyl-sulfoxide.

2. Production of Ascites Fluid Containing Monoclonal Antibodies. Frozen hybridoma cells prepared as described hereinabove are thawed and placed into expansion culture. Viable hybridoma cells are inoculated intraperitoneally into Pristane treated mice. Ascitic fluid is removed from the mice, pooled, filtered through a 0.2μ filter and subjected to an immunoglobulin class G (IgG) analysis to determine the volume of the Protein A column required for the purification.

3. Purification of Monoclonal Antibodies From Ascites Fluid. Briefly, filtered and thawed ascites fluid is mixed with an equal volume of Protein A sepharose binding buffer (1.5 M glycine, 3.0M NaCl, pH 8.9) and refiltered through a 0.2μ filter. The volume of the Protein A column is determined by the quantity of IgG present in the ascites fluid. The eluate then is dialyzed against PBS pH 7.2 overnight at 2–8° C. The dialyzed monoclonal antibody is sterile filtered and dispensed in aliquots. The immunoreactivity of the purified monoclonal antibody is confirmed by determining its ability to specifically bind to the peptide used as the immunogen by use of the EIA microtiter plate assay procedure of Example 17. The specificity of the purified monoclonal antibody is confirmed by determining its lack of binding to irrelevant peptides such as peptides of PS108 not used as the immunogen. The purified anti-PS108 monoclonal thus prepared and characterized is placed at either 2–8° C. for short term storage or at −80° C. for long term storage.

4. Further Characterization of Monoclonal Antibody. The isotype and subtype of the monoclonal antibody produced as described hereinabove can be determined using commercially available kits (available from Amersham. Inc., Arlington Heights, Ill.). Stability testing also can be performed on the monoclonal antibody by placing an aliquot of the monoclonal antibody in continuous storage at 2–8° C. and assaying optical density (OD) readings throughout the course of a given period of time.

C. Use of Recombinant Proteins as Immunogens. It is within the scope of the present invention that recombinant proteins made as described herein can be utilized as immunogens in the production of polyclonal and monoclonal antibodies, with corresponding changes in reagents and techniques known to those skilled in the art.

Example 15

Purification of TNF-Gamma Peptide Specific Antibodies From Serum

Immune sera is affinity purified using immobilized synthetic peptides by methods known in the art. Antiserum produced against a peptide as described in Example 10 is affinity purified in a variety of ways. An IgG fraction is obtained by passing the diluted, crude antiserum over a Protein A column (Affi-Gel protein A, Bio-Rad, Hercules, Calif.). Elution with Binding Buffer supplied by the manufacturer removes all proteins that are not immunoglobulins. Elution with pH 3 buffered glycine, 0.1M gives an immunoglobulin preparation that is substantially free of albumin and other serum proteins.

Immunoaffinity chromatography is performed to obtain a preparation with a higher fraction of specific antigen-binding antibody. The peptide used to raise the antiserum is immobilized on a chromatography resin and the specific antibodies directed against its epitopes are adsorbed to the resin. After washing away non-binding components, the specific antibodies are eluted with 0.1M glycine buffer, pH 2.3; antibody fractions are immediately neutralized with 1.0M Tris buffer, pH 8.0, to preserve immunoreactivity. The resin chosen depends on the reactive groups present in the peptide. If the peptide has an amino group, a resin such as Affi-Gel 10 or Affi-Gel 15 is used (Bio-Rad, Hercules, Calif.). If coupling through a carboxy group on the peptide is desired, Affi-Gel 102 can be used (Bio-Rad, Hercules, Calif.). If the peptide has a free sulfhydryl group, an organomercurial resin such as Affi-Gel 501 can be used (Bio-Rad, Hercules, Calif.).

Alternatively, spleens can be harvested and used in the production of hybridomas to produce monoclonal antibodies.

Example 16

Western Blotting of Tissue Samples

Tissue samples are homogenized in SDS-PAGE sample buffer (50 mM Tris-HCl, pH 6.8, 100 mM dithiothreitol, 2% SDS, 0.1% bromophenol blue, 10glycerol), heated at 100° C. for 10 min and run on a 14% SDS-PAGE with a 25 mM Tris-HCl, pH 8.3, 250 mM Glycine, 0.1% SDS running buffer. The proteins are electrophoretically transferred to nitrocellulose in a transfer buffer containing 39 mM glycine, 48 mM Tris-HCl, pH 8.3, 0.037% SDS, 20% methanol. The nitrocellulose is dried at room temperature for 60 min and then blocked with a PBS solution containing either bovine serum albumin or 5% nonfat dried milk for 2 h at 4° C.

The filter is placed in a heat-sealable plastic bag containing a solution of 5% nonfat dried milk in PBS with a 1:100 to 1:2000 dilution of affinity purified anti-EST peptide antibodies (see example 15), incubated at 4° C. for 2 h, followed by 3 10 min washes in PBS. An alkaline phosphatase conjugated secondary antibody, anti-mouse/rabbit IgG, is added at a 1:200 to 1:2000 dilution to the filter in a 150 mM NaCl, 50 mM Tris-HCl, pH 7.5 buffer and incubated for 1 h at room temperature.

The bands are visualized upon the addition and development of a chromogenic substrate such as 5-bromo-4-chloro-3-indolyl phosphate/nitro blue tetrazolium (BCIP/NBT). This chromogenic solution contains 0.033% NBT and 0.016% BCIP in a solution containing 100 mM NaCl, 5 mM $MgCl_2$ and 100 mM Tris-HCl, pH 9.5. The filter is incubated in the solution at room temperature until the bands develop to the desired intensity. Development is stopped in a PBS buffer containing 2 mM EDTA. Molecular mass determination is made based upon the mobility of pre-stained molecular weight standards (Rainbow markers, Amersham, Arlington Heights, Ill.).

Example 17

EIA Microtiter Plate Assay

To demonstrate how relative immunoreactivity for EST synthetic peptides is measured, wells of 96-well microtiter plates (Dynatec Immunolon 4 polystyrene) are coated for 16 h at 4° C. with 100 μl of the EST peptide at the following concentrations: 500 μM, 50 μM, 5 μM, 0.5 μM, 0.05 μM, and 0.005 μM. The buffer used for the application of these peptides is 100 mM morpholino-ethane sulfonic acid, pH 5.5. The EST peptides coated wells are then washed 3 times with wash buffer (8 mM sodium phosphate, 2 mM potassium phosphate, 140 mM sodium chloride, 10 mM potassium chloride, 0.05% Tween 20, 0.1% bovine serum albumin, pH 7.4).

The wells then are blocked for 1 h at room temperature with 9% w/v of Carnation skim milk powder in phosphate buffered saline (8 mM sodium phosphate, 2 mM potassium phosphate, 140 mM sodium chloride, 10 mM potassium chloride, pH 7.4). The wells next are washed 3 times with wash buffer.

The test specimen or control (mouse or rabbit antiserum) is diluted 150-fold with 4.5% Carnation skim milk powder in PBS. Then, 100 μl of this sample are incubated in the wells at 37° C. for 1 h, followed by 3 washes with wash buffer.

Horseradish peroxidase conjugated goat anti-mouse/rabbit IgG is used as a second antibody label to bind with the anti-EST-antibody/EST antigen complex formed in positive wells. 100 μL of HRPO-goat anti-mouse/rabbit IgG conjugate at a dilution of about 1:5000 in wash buffer are added to each well and incubated at room temperature for 1 h. The wells are washed 3 times with wash buffer.

Positive wells are identified by the absorbance readings at 405 nm after exposure of the wells to 100 μL of ABTS solution (2,2'-azinobis-[3-ethylbenzothizoline-6-sulfonic acid] diammonium salt) (Pierce Chemical Co., Rockford, Ill., U.S.A.). Alternatively, color development can be achieved with the addition to each well of 100 μl of a solution of o-phenylene diamine (OPD) in hydrogen peroxide, and a 10 min incubation at room temperature. The color development reaction is quenched with 100 μl of 1N sulfuric acid. The colors in the wells are read as absorbance with a Dynatech MR5000 plate reader at 490 nm and 630 nm wavelengths. A positive signal is indicative the presence of anti-EST peptide antibodies.

Example 18

Coating of Solid Phase Particles

A. Coating of Microparticles with Anti-EST Peptide Antibody. Affinity purified anti-EST peptide antibodies (see example 15) are coated onto microparticles which may include polystyrene, carboxylated polystyrene, polymethylacrylate or similar particles with a radius in the range of about 0.1 to 20 μm. Microparticles may be either passively or actively coated. One method is coating of EDAC (1-(3-dimethylaminopropyl)-3-ethylcarbodiimide hydrochloride (Aldrich Chemical. Co., Milwaukee, Wis.) activated carboxylated latex microparticles with anti-EST antibody. Briefly, a final 0.375% solid solution of resin washed carboxylated latex microparticles are mixed in a solution containing 50 mM MES buffer, pH 4.0 and 150 mg/l of affinity purified anti-EST antibody (see example 15) for 15 min in an appropriate container. EDAC coupling agent is added to a final concentration of 5.5 μg/ml to the mixture and mixed for 2.5 h at room temperature.

The microparticles then are washed with 8 volumes of a Tween 20®/sodium phosphate, pH 7.2 wash buffer by tangential flow filtration using a 0.2 μm Microgon Filtration module. Washed microparticles are stored in an appropriate buffer, usually containing a dilute surfactant and irrelevant protein as a blocking agent, until needed.

B. Coating of ¼ inch Beads. Anti-EST antibodies also may be coated on the surface of ¼ inch polystyrene beads by routine methods known in the art (Snitman et al, U.S. Pat. No. 5,273,882, incorporated herein by reference) and used in competitive binding or EIA sandwich assays. Polystyrene beads are first cleaned by ultrasonicating them for about 15 seconds in 10 mM NaHCO$_3$ buffer at pH 8.0. The beads are then washed in deionized water until all fines are removed. Beads are then immersed in an antibody solution in 10 mM carbonate buffer, pH 8 to 9.5. The antibody solution can be as dilute as 1 μg/ml in the case of high affinity monoclonal antibodies or as concentrated as about 500 μg/ml for polyclonal antibodies which have not been affinity purified. Beads are coated for at least 12 hours at room temperature and then washed with deionized water. Beads may be dried or stored wet. They may be overcoated with protein stabilizers (sucrose) or non-specific binding blockers (irrelevant proteins, Carnation skim milk, or the like).

Example 19

Microparticle Enzyme Immunoassay (MEIA)

EST proteins and peptides are detected using a standard commercialized antigen competition EIA assay or polyclonal antibody sandwich EIA assay on the IMx® Analyzer (Abbott Laboratories, Abbott Park, Ill.). Briefly, samples suspected of containing the EST protein are incubated in the presence of anti-EST coated microparticles (see example 16). The microparticles are washed and secondary polyclonal anti-EST antibodies conjugated with detectable entities (i.e., alkaline phosphatase) are added and incubated with the microparticles. The microparticles are washed and the bound antibody/antigen/antibody complexes are detected by adding a substrate (i.e. 4-methyl umbelliferyl phosphate) (MUP) that will react with the secondary conjugated antibody to generate a detectable signal. An elevated signal, indicating the presence of EST protein, is diagnostic of cancer.

Competitive binding assay uses a detectably labeled peptide that generates a specific background signal on the IMx® analyzer when the peptide is bound to an anti-peptide antibody coated microparticle. The labeled peptide also is added to the microparticles in the presence of patient samples suspected of containing the EST protein. The EST protein in the patient sample will compete with the labeled EST peptide for binding sites on the microparticle resulting in lowered IMx® signals. A lowered signal, indicating the presence of EST protein in the patient sample, is indicative of the presence of the TNF-gamma gene product, suggesting the diagnosis of inflammatory disease.

The TNF-gamma gene polynucleotides and the proteins encoded therein which are provided and discussed hereinabove therefore are thought to be useful as markers of TNF-gamma associated disease. Tests based upon the appearance of this marker in a test sample such as blood, plasma or serum can provide low cost, non-invasive, diagnostic information to aid the physician to make a diagnosis of cancer, to help select a therapy protocol, or to monitor the success of the chosen therapy. This marker may appear in readily accessible body fluids such as blood, urine or stool as antigens derived from the diseased tissue which are detectable by immunological methods. This marker may be elevated in a disease state, altered in a disease state, or be a normal protein which appears in an inappropriate body compartment. Also, the TNF-gamma gene polynucleotides and the proteins encoded therein provided by the present invention are useful for treating a variety of disorders.

What is claimed is:

1. A method of detecting the presence of a target polynucleotide of TNF-gamma in a test sample, comprising:

(a) contacting said test samples, under conditions such that binding occurs, with at least one polynucleotide sequence corresponding to SEQ ID NO:1 or a full-length complement thereof, wherein said at least one polynucleotide sequence or said full-length complement thereof is conjugated to a detectable label capable of generating a measurable signal;

(b) determining, subsequent to detection of said signal, whether at least one polynucleotide sequence of said test sample, which binds to said at least one polynucleotide sequence corresponding to SEQ ID NO:1 or said full-length complement thereof, has at least 70% identity to SEQ ID NO:1 or said full-length complement thereof, wherein the presence of said at least one polynucleotide sequence having at least 70% identity to SEQ ID NO:1 or said full-length complement thereof indicates target TNF-gamma polynucleotide in said test sample.

2. The method of claim 1 wherein said at least one polynucleotide sequence corresponding to SEQ ID NO:1 or full-length complement thereof is attached to a solid phase prior to performing step (a).

3. A method of detecting a target TNF-gamma polynucleotide in a test sample suspected of containing said target, comprising:
   (a) contacting polynucleotide sequences of said test sample, under conditions such that hybridization may occur, with at least one TNF-gamma oligonucleotide sequence corresponding to SEQ ID NO:1 or a full-length complement thereof as a sense primer and with at least one TNF-gamma oligonucleotide sequence corresponding to SEQ ID NO:1 or said full-length complement thereof as an anti-sense primer and amplifying the same to obtain a first stage reaction product;
   (b) contacting said first stage reaction product with at least one other TNF-gamma oligonucleotide sequence, with the proviso that said other TNF-gamma oligonucleotide sequence is located 3' to the TNF-gamma oligonucleotide sequences utilized in step (a) and is complementary to said first stage reaction product; and
   (c) detecting said target TNF-gamma polynucleotide.

4. The method of claim 3, wherein said test sample is reacted with a solid phase prior to performing step (a) or step (b) or step (c).

5. The method of claim 3, wherein said detection step comprises utilizing a detectable label capable of generating a measurable signal.

6. The method of claim 5, wherein said detectable label is conjugated to said TNF-gamma oligonucleotide sequences and said label is reacted to a solid phase.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 1187 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:1:

```
ATTTCTCCTT GCGTAACAAC CTTCTTCCCT TCTGCACCAC TGCCCGTACCCTTACCCGCC     60
CCGCCACCTC CTTGCTACCC CACTCTTGAA ACCACAGCTG TTGGCAGGGTCCCCAGCTCA    120
TGCCAGCCTC ATCTCCTTTC TTGCTAGCCC CCAAAGGGCC TCCAGGCAACATGGGGGCC     180
CAGTCAGAGA GCCGGCACTC TCAGTTGCCC TCTGGTTGAG TTGGGGGCAGCTCTGGGGG     240
CCGTGGCTTG TGCCATGGCT CTGCTGACCC AACAAACAGA GCTGCAGAGCCTCAGGAGAG    300
AGGTGAGCCG GCTGCAGGGG ACAGGAGGCC CCTCCCAGAA TGGGGAAGGGTATCCCTGGC    360
AGAGTCTCCC GGAGCAGAGT TCCGATGCCC TGGAAGCCTG GGAGAATGGGGAGAGATCCC    420
GGAAAAGGAG AGCAGTGCTC ACCCAAAAAC AGAAGAAGCA GCACTCTGTCCTGCACCTGG    480
TTCCCATTAA CGCCACCTCC AAGGATGACT CCGATGTGAC AGAGGTGATGTGGCAACCAG    540
CTCTTAGGCG TGGGAGAGGC CTACAGGCCC AAGGATATGG TGTCCGAATCCAGGATGCTG    600
GAGTTTATCT GCTGTATAGC CAGGTCCTGT TTCAAGACGT GACTTTCACCATGGGTCAGG    660
TGGTGTCTCG AGAAGGCCAA GGAAGGCAGG AGACTCTATT CCGATGTATAAGAAGTATGC    720
CCTCCCACCC GGACCGGGCC TACAACAGCT GCTATAGCGC AGGTGTCTTCCATTTACACC    780
AAGGGGATAT TCTGAGTGTC ATAATTCCCC GGGCAAGGGC GAAACTTAACCTCTCTCCAC    840
ATGGAACCTT CCTGGGGTTT GTGAAACTGT GATTGTGTTA TAAAAAGTGGCTCCCAGCTT    900
GGAAGACCAG GGTGGGTACA TACTGGAGAC AGCCAAGAGC TGAGTATATAAAGGAGAGGG    960
AATGTGCAGG AACAGAGGCG TCTTCCTGGG TTTGGCTCCC CGTTCCTCACTTTTCCCTTT   1020
TCATTCCCAC CCCCTAGACT TTGATTTTAC GGATATCTTG CTTCTGTTCCCCATGGAGCT   1080
CCGAATTCTT GCGTGTGTGT AGATGAGGGG CGGGGACGG GCGCCAGGCATTGTTCAGAC    1140
CTGGTCGGGG CCCACTGGAA GCATCCAGAA CAGCACCACC ATCTAGC                 1187
```

(2) INFORMATION FOR SEQ ID NO:2:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
            20                  25                  30
```

-continued

```
Leu Ser Trp Gly Ala Ala Leu Gly Ala Val Ala Cys Ala Met Ala Leu
            35                  40                  45

Leu Thr Gln Gln Thr Glu Leu Gln Ser Leu Arg Arg Glu Val Ser Arg
 50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
                100                 105                 110

Lys Gln His Ser Val Leu His Leu Val Pro Ile Asn Ala Thr Ser Lys
                115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
                180                 185                 190

Leu Phe Arg Cys Ile Arg Ser Met Pro Ser His Pro Asp Arg Ala Tyr
            195                 200                 205

Asn Ser Cys Tyr Ser Ala Gly Val Phe His Leu His Gln Gly Asp Ile
210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

(2) INFORMATION FOR SEQ ID NO:3:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

Arg Ala Val Leu Thr Gln Lys Gln Lys Lys Gln His Ser Val Leu His
 1               5                  10                  15

Leu Val Pro Ile Asn Ala Thr Ser Lys Asp Asp Ser Asp Val Thr Glu
                20                  25                  30

Val Met Trp Gln Pro Ala Leu Arg Arg Gly Arg Gly Leu Gln Ala Gln
            35                  40                  45

Gly Tyr Gly Val Arg Ile Gln Asp Ala Gly Val Tyr Leu Leu Tyr Ser
 50                  55                  60

Gln Val Leu Phe Gln Asp Val Thr Phe Thr Met Gly Gln Val Val Ser
 65                  70                  75                  80

Arg Glu Gly Gln Gly Arg Gln Glu Thr Leu Phe Arg Cys Ile Arg Ser
                 85                  90                  95

Met Pro Ser His Pro Asp Arg Ala Tyr Asn Ser Cys Tyr Ser Ala Gly
                100                 105                 110

Val Phe His Leu His Gln Gly Asp Ile Leu Ser Val Ile Ile Pro Arg
            115                 120                 125
```

```
Ala Arg Ala Lys Leu Asn Leu Ser Pro His Gly Thr Phe Leu Gly Phe
    130                 135                 140

Val Lys Leu
145

(2) INFORMATION FOR SEQ ID NO:4:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:4:

Met Lys Trp Val Thr Phe Ile Ser Leu Leu Phe Leu Phe Ser Ser Ala
 1               5                  10                  15

Tyr Ser Arg Gly Val Phe Arg Arg
             20

(2) INFORMATION FOR SEQ ID NO:5:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:5:

Asp Tyr Lys Asp Asp Asp Asp Lys
 1               5

(2) INFORMATION FOR SEQ ID NO:6:

(i) SEQUENCE CHARACTERISTICS:
         (A) LENGTH: 233 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:6:

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
             20                  25                  30

Leu Ser Leu Phe Ser Phe Leu Ile Val Ala Gly Ala Thr Thr Leu Phe
         35                  40                  45

Cys Leu Leu His Phe Gly Val Ile Gly Pro Gln Arg Glu Glu Phe Pro
     50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
             100                 105                 110

Leu Ala Asn Gly Val Glu Leu Arg Asp Asn Gln Leu Val Val Pro Ser
         115                 120                 125

Glu Gly Leu Tyr Leu Ile Tyr Ser Gln Val Leu Phe Lys Gly Gln Gly
```

```
            130                 135                 140
Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
                210                 215                 220

Gln Val Tyr Phe Gly Ile Ile Ala Leu
225                 230

(2) INFORMATION FOR SEQ ID NO:7:

(i) SEQUENCE CHARACTERISTICS:
         (A) LENGTH: 235 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:7:

Met Ser Thr Glu Ser Met Ile Arg Asp Val Glu Leu Ala Glu Ala
1                   5                  10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
                35                  40                  45

Cys Leu Leu Asn Phe Gly Val Ile Gly Pro Gln Arg Asp Glu Lys Phe
                50                  55                  60

Pro Asn Gly Leu Pro Leu Ile Ser Ser Met Ala Gln Thr Leu Thr Leu
65                  70                  75                  80

Arg Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
                100                 105                 110

Asn Ala Leu Leu Ala Asn Gly Met Asp Leu Lys Asp Asn Gln Leu Val
                115                 120                 125

Val Pro Ala Asp Gly Leu Tyr Leu Val Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
                180                 185                 190

Tyr Glu Pro Ile Tyr Leu Gly Gly Val Phe Gln Leu Glu Lys Gly Asp
                195                 200                 205

Gln Leu Ser Ala Glu Val Asn Leu Pro Lys Tyr Leu Asp Phe Ala Glu
                210                 215                 220

Ser Gly Gln Val Tyr Phe Gly Val Ile Ala Leu
225                 230                 235
```

(2) INFORMATION FOR SEQ ID NO:8:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
        50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
    195                 200                 205
```

(2) INFORMATION FOR SEQ ID NO:9:

(i) SEQUENCE CHARACTERISTICS:
        (A) LENGTH: 244 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
        50                  55                  60

Ala Gln Gln Gly Leu Gly Phe Gln Lys Leu Pro Glu Glu Glu Pro Glu
65                  70                  75                  80
```

-continued

```
Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
            115                 120                 125

Gln Asp Gly Leu Tyr Tyr Leu Tyr Cys Leu Val Gly Tyr Arg Gly Arg
130                 135                 140

Ala Pro Pro Gly Gly Asp Pro Gln Gly Arg Ser Val Thr Leu Arg
145                 150                 155                 160

Ser Ser Leu Tyr Arg Ala Gly Ala Tyr Gly Pro Gly Thr Pro Glu
            165                 170                 175

Leu Leu Leu Glu Gly Ala Glu Thr Thr Pro Val Leu Asp Pro Ala
            180                 185                 190

Arg Arg Gln Gly Tyr Gly Pro Leu Trp Tyr Thr Ser Val Gly Phe Gly
            195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly
```

(2) INFORMATION FOR SEQ ID NO:10:

(i) SEQUENCE CHARACTERISTICS:
       (A) LENGTH: 281 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:10:

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
            85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
```

```
                    180                 185                 190
Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280
```

(2) INFORMATION FOR SEQ ID NO:11:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:11:

```
AGCTCGGAAT TCCGAGCTTG GATCCTCTAG AGCGGCCGCC GACTAGTGAG CTCGTCGACC     60

CGGGAATT                                                              68
```

(2) INFORMATION FOR SEQ ID NO:12:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:12:

```
AATTAATTCC CGGGTCGACG AGCTCACTAG TCGGCGGCCG CTCTAGAGGA TCCAAGCTCG     60

GAATTCCG                                                              68
```

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

Ser Asn Glu Leu